(12) United States Patent
Atterbury et al.

(10) Patent No.: US 12,133,972 B2
(45) Date of Patent: Nov. 5, 2024

(54) SYSTEMS, DEVICES, AND PROCESSES FOR DELIVERY OF THERAPEUTIC FLUIDS

(71) Applicant: Eli Lilly and Company, Indianapolis, IN (US)

(72) Inventors: William Godwin Atterbury, Columbus, OH (US); Corrie Jo Bennison, Lewis Center, OH (US); Jeffrey Richard Held, Columbus, OH (US); David Arthur Holley, Lancaster, OH (US); Noah John Scott Lemire, Columbus, OH (US); Beverly Anne Piatt, Columbus, OH (US); John Paul Tallarico, Powell, OH (US)

(73) Assignee: Eli Lilly and Company, Indianapolis, IN (US)

( * ) Notice: Subject to any disclaimer, the term of this patent is extended or adjusted under 35 U.S.C. 154(b) by 825 days.

(21) Appl. No.: 17/311,117

(22) PCT Filed: Dec. 12, 2019

(86) PCT No.: PCT/US2019/066035
§ 371 (c)(1),
(2) Date: Jun. 4, 2021

(87) PCT Pub. No.: WO2020/131577
PCT Pub. Date: Jun. 25, 2020

(65) Prior Publication Data
US 2021/0361880 A1 Nov. 25, 2021

Related U.S. Application Data

(60) Provisional application No. 62/781,670, filed on Dec. 19, 2018.

(51) Int. Cl.
*A61M 5/315* (2006.01)
*A61M 5/19* (2006.01)
(Continued)

(52) U.S. Cl.
CPC .......... *A61M 5/31586* (2013.01); *A61M 5/19* (2013.01); *A61M 5/2033* (2013.01);
(Continued)

(58) Field of Classification Search
None
See application file for complete search history.

(56) References Cited

U.S. PATENT DOCUMENTS 2,390,246 A 12/1945 Folkman
2,446,429 A 8/1948 Nelson et al.
(Continued)

FOREIGN PATENT DOCUMENTS

DE 3809482 10/1989
EP 0666084 8/1995
(Continued)

OTHER PUBLICATIONS

International Search Report of the International Searching Authority pertaining to International Application No. PCT/US2019/066035; Date of Mailing: Apr. 2, 2020; 7 pages.
(Continued)

*Primary Examiner* — Manuel A Mendez
(74) *Attorney, Agent, or Firm* — Jonathan C. Anderson

(57) ABSTRACT

A therapeutic agent delivery system (10) includes a housing (16) and a drive wheel (38) rotatably carried by the housing. A plunger rod (50) may be rotatable with the drive wheel relative to the housing from a first rotational configuration to a second rotational configuration. The plunger rod may be translatable relative to the housing from a first translational configuration to a second translational configuration. A plunger restraint (58) may maintain the plunger rod in the first translational configuration when the plunger rod is disposed in the first rotational configuration. The plunger restraint may permit the plunger rod to translate to the
(Continued)

second translational configuration when the plunger rod is disposed in the second rotational configuration. A needle may move from a stowed configuration to a deployed configuration by the plunger rod when the plunger rod moves from the first translational configuration to the second translational configuration.

20 Claims, 33 Drawing Sheets

(51) Int. Cl.
A61M 5/20 (2006.01)
A61M 5/32 (2006.01)
(52) U.S. Cl.
CPC ...... *A61M 5/2046* (2013.01); *A61M 5/31505* (2013.01); *A61M 5/3232* (2013.01); *A61M 5/3287* (2013.01); *A61M 2005/2026* (2013.01)

(56) References Cited

U.S. PATENT DOCUMENTS

| | | | |
|---|---|---|---|
| 2,833,745 A | 5/1958 | Fikentscher |
| 2,923,243 A | 2/1960 | Crockford et al. |
| 3,405,845 A | 10/1968 | Cook et al. |
| 3,467,526 A | 9/1969 | Mitchell et al. |
| 3,556,803 A | 1/1971 | Ehrreich, III et al. |
| 3,594,410 A | 7/1971 | Cohen et al. |
| 3,754,993 A | 8/1973 | Oguchi et al. |
| 3,773,111 A | 11/1973 | Dunn |
| 3,968,796 A | 7/1976 | Baker |
| 4,031,889 A | 6/1977 | Pike |
| 4,203,441 A | 5/1980 | Theeuwes |
| 4,675,174 A | 6/1987 | Eckenhoff |
| 4,744,786 A | 5/1988 | Hooven |
| 4,785,972 A | 11/1988 | LeFevre |
| 4,795,748 A | 1/1989 | Ross et al. |
| 5,034,114 A | 7/1991 | Kukin |
| 5,062,834 A | 11/1991 | Gross et al. |
| 5,151,093 A | 9/1992 | Theeuwes et al. |
| 5,167,641 A | 12/1992 | Schmitz |
| 5,304,128 A | 4/1994 | Haber et al. |
| 5,312,389 A | 5/1994 | Theeuwes et al. |
| 5,398,850 A | 3/1995 | Sancoff et al. |
| 5,478,316 A | 12/1995 | Bitdinger et al. |
| 5,518,145 A | 5/1996 | Chen |
| 5,540,665 A | 7/1996 | Mercado et al. |
| 5,645,824 A | 7/1997 | Lim et al. |
| 5,700,245 A | 12/1997 | Sancoff et al. |
| 5,855,761 A | 1/1999 | Joshi |
| 5,858,001 A | 1/1999 | Tsals et al. |
| 5,871,125 A | 2/1999 | Gross |
| 5,891,087 A | 4/1999 | Ohtani et al. |
| 5,941,857 A | 8/1999 | Nguyen et al. |
| 5,992,700 A | 11/1999 | McGlothlin et al. |
| 6,086,568 A | 7/2000 | Caizza |
| 6,086,569 A | 7/2000 | Schweizer |
| 6,156,014 A | 12/2000 | Petersen et al. |
| 6,270,479 B1 | 8/2001 | Bergens et al. |
| 6,431,468 B1 | 8/2002 | Brown et al. |
| 6,575,961 B2 | 6/2003 | Joshi |
| 6,786,365 B2 | 9/2004 | Kim |
| 6,830,560 B1 | 12/2004 | Gross et al. |
| 6,913,593 B1 | 7/2005 | Alexandre et al. |
| 6,964,356 B2 | 11/2005 | Kim |
| 7,632,245 B1 | 12/2009 | Cowan et al. |
| 7,717,877 B2 | 5/2010 | Lavi et al. |
| 7,753,884 B2 | 7/2010 | Gallnböck |
| 7,985,309 B2 | 7/2011 | Kim |
| 7,988,663 B2 | 8/2011 | Schiller et al. |
| 8,157,769 B2 | 4/2012 | Cabiri |
| 8,353,426 B2 | 1/2013 | Wold et al. |
| 8,353,679 B2 | 1/2013 | Yamamoto et al. |
| 9,233,209 B2 | 1/2016 | Markussen et al. |
| 9,321,581 B2 | 4/2016 | Bennison et al. |
| 9,402,957 B2 | 8/2016 | Adams et al. |
| 9,795,740 B2 | 10/2017 | Heintz et al. |
| 2001/0025168 A1 | 9/2001 | Gross et al. |
| 2001/0050085 A1 | 12/2001 | Knudson et al. |
| 2002/0156461 A1 | 10/2002 | Joshi |
| 2003/0168480 A1 | 9/2003 | Kim |
| 2004/0249339 A1 | 12/2004 | Willis et al. |
| 2005/0006401 A1 | 1/2005 | Kim |
| 2005/0063766 A1 | 3/2005 | Chen et al. |
| 2005/0187522 A1 | 8/2005 | Miller |
| 2006/0235264 A1 | 10/2006 | Vassallo |
| 2007/0088268 A1 | 4/2007 | Edwards |
| 2007/0088337 A1 | 4/2007 | Lautenbach |
| 2007/0173770 A1 | 7/2007 | Stamp |
| 2007/0228071 A1 | 10/2007 | Kamen et al. |
| 2007/0233001 A1 | 10/2007 | Burroughs et al. |
| 2008/0066766 A1 | 3/2008 | Paraschac et al. |
| 2008/0147006 A1 | 6/2008 | Brunnberg et al. |
| 2008/0233029 A1 | 9/2008 | Fan et al. |
| 2008/0257915 A1 | 10/2008 | Wold |
| 2008/0262427 A1 | 10/2008 | Hommann |
| 2009/0093787 A1 | 4/2009 | Barbour |
| 2009/0131860 A1 | 5/2009 | Nielsen |
| 2009/0227942 A1 | 9/2009 | Stroem Hansen et al. |
| 2009/0259176 A1 | 10/2009 | Yairi |
| 2009/0259179 A1 | 10/2009 | Hillios et al. |
| 2009/0292246 A1 | 11/2009 | Slate et al. |
| 2010/0030152 A1 | 2/2010 | Lee et al. |
| 2010/0063444 A1 | 3/2010 | Wikner |
| 2010/0069846 A1 | 3/2010 | Stamp |
| 2010/0137808 A1 | 6/2010 | Wilmot et al. |
| 2010/0152660 A1 | 6/2010 | Mack et al. |
| 2010/0174225 A1 | 7/2010 | Pesach et al. |
| 2010/0292653 A1 | 11/2010 | Maritan |
| 2011/0054390 A1 | 3/2011 | Searle et al. |
| 2011/0092906 A1 | 4/2011 | Bottger et al. |
| 2011/0270188 A1 | 11/2011 | Caffey et al. |
| 2011/0272271 A1 | 11/2011 | Hong et al. |
| 2012/0078216 A1 | 3/2012 | Smith et al. |
| 2012/0130313 A1 | 5/2012 | Byerly et al. |
| 2013/0253472 A1 | 9/2013 | Cabiri |
| 2013/0324934 A1 | 12/2013 | Holmqvist et al. |
| 2014/0012229 A1 | 1/2014 | Bokelman et al. |
| 2014/0103075 A1 | 4/2014 | Bennison et al. |
| 2014/0180218 A1 | 6/2014 | Fourt et al. |
| 2014/0257193 A1 | 9/2014 | Boström et al. |
| 2014/0309591 A1 | 10/2014 | Holmqvist |
| 2014/0330216 A1 | 11/2014 | Weaver et al. |
| 2015/0045729 A1 | 2/2015 | Denzer et al. |
| 2015/0157790 A1 | 6/2015 | Henderson et al. |
| 2015/0314070 A1 | 11/2015 | Heintz et al. |
| 2015/0363097 A1 | 12/2015 | Draper et al. |
| 2016/0156060 A1 | 6/2016 | Hamelers et al. |
| 2016/0213846 A1 | 7/2016 | Bennison et al. |
| 2016/0213847 A1 | 7/2016 | Bennison et al. |
| 2016/0213859 A1 | 7/2016 | Sadowski et al. |
| 2017/0014575 A1 | 1/2017 | Hansen et al. |
| 2017/0098058 A1 | 4/2017 | McCullough et al. |
| 2017/0224926 A1 | 8/2017 | Dennis, Jr. et al. |
| 2017/0281877 A1 | 10/2017 | Marlin et al. |
| 2017/0354779 A1 | 12/2017 | Atterbury et al. |
| 2017/0354785 A1* | 12/2017 | Gazeley ............. A61M 5/3232 |
| 2018/0021521 A1 | 1/2018 | Sanchez |
| 2018/0110926 A1 | 4/2018 | Schrul et al. |

FOREIGN PATENT DOCUMENTS

| | | |
|---|---|---|
| EP | 2221076 | 8/2010 |
| EP | 2489387 | 8/2012 |
| EP | 2624884 | 8/2013 |
| JP | H03178671 | 8/1991 |
| WO | 92019571 | 11/1992 |
| WO | 95001198 | 1/1995 |
| WO | 95023641 | 9/1995 |
| WO | 97028750 | 8/1997 |
| WO | 99012593 | 3/1999 |
| WO | 99022790 | 5/1999 |
| WO | 99062576 | 12/1999 |

(56) References Cited

FOREIGN PATENT DOCUMENTS

| | | |
|---|---|---|
| WO | 01000270 | 1/2001 |
| WO | 07071485 | 6/2007 |
| WO | 2009040602 | 4/2009 |
| WO | 09116045 | 9/2009 |
| WO | 09144726 | 12/2009 |
| WO | 2011039212 | 4/2011 |
| WO | 2011075099 | 6/2011 |
| WO | 2012122643 | 9/2012 |
| WO | 2013065055 | 5/2013 |
| WO | 2013092670 | 6/2013 |
| WO | 14059444 | 4/2014 |
| WO | 2015160600 | 10/2015 |
| WO | 2016033507 | 3/2016 |
| WO | 2017214405 | 12/2017 |
| WO | 2018152018 | 8/2018 |

OTHER PUBLICATIONS

Written Opinion of the International Searching Authority pertaining to International Application No. PCT/US2019/066035; Date of Mailing: Apr. 2, 2020; 7 pages.
"Development of an On-Demand, Generic, Drug-Delivery System," Southern Research Institute, 2000 Ninth Avenue South, Birmingham, AL 35255-5305 Aug. 6, 1985; 30 pages.
Good, Brian T., et al., "An Effervescent Reaction Micropump for Portable Microfluidic Systems," *Lab Chip*, 2006, 6, 659-66; 8 pages.

* cited by examiner

SYSTEMS, DEVICES, AND PROCESSES FOR DELIVERY OF THERAPEUTIC FLUIDS

CROSS-REFERENCE TO RELATED APPLICATIONS

This application is a National Stage of International Application No. PCT/US2019/066035, filed Dec. 12, 2019, which claims priority to U.S. Provisional Application No. 62/781,670, filed Dec. 19, 2018, the disclosures of which are hereby expressly incorporated by reference herein in their entirety.

FIELD OF THE DISCLOSURE

The present disclosure relates to processes and devices for parenteral delivery of therapeutic agents. More particularly, the present disclosure relates to processes and devices for parenteral delivery of high-viscosity therapeutic fluids (for example, protein therapeutics).

BACKGROUND OF THE DISCLOSURE

Protein therapeutics is an emerging class of drug therapy that provides treatment for a broad range of diseases, such as autoimmune disorders, cardiovascular diseases, diabetes, and cancer. A common delivery method for some protein therapeutics, such as monoclonal antibodies for example, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes and injection pens requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe typically ranges from 0.3 milliliters to 25 milliliters. Thus, depending on the drug, to deliver the same amount of therapeutic proteins in an injection device the drug concentration may have to increase by a factor of 40 or more. Further, injection therapy is moving towards smaller needle diameters and faster delivery times for purposes of patient comfort and compliance.

The high viscosity associated with such therapeutic formulations and the high forces needed to push such formulations through a parenteral device present a challenge in protein therapeutic delivery. Formulations with absolute viscosities above 40-60 centipoise (cP), for example, may be difficult to deliver by conventional spring driven auto-injectors. A large amount of energy must be stored in the spring to reliably deliver high-viscosity fluids. If not properly designed, this stored energy may cause damage to the plastic parts due to creep, which is the tendency of the plastic part to permanently deform under stress. Further, the generated pressure versus time profile of such a spring driven auto-injector may not be easily modifiable, which reduces the ability to adjust pressure to meet delivery needs.

It would be desirable to provide processes and devices by which a therapeutic fluid, in particular a high-viscosity fluid, is self-administered in a reasonable time and with a limited injection space. These processes and devices may be used to deliver high-concentration protein, high-viscosity pharmaceutical formulations, or other therapeutic fluids.

SUMMARY

According to an exemplary embodiment of the present disclosure, a therapeutic agent delivery system includes a housing, and a drive wheel is rotatably carried by the housing. A plunger rod is rotatable with the drive wheel relative to the housing from a first rotational configuration to a second rotational configuration. The plunger rod is translatable relative to the housing from a first translational configuration to a second translational configuration. A plunger restraint maintains the plunger rod in the first translational configuration when the plunger rod is disposed in the first rotational configuration. The plunger restraint permits the plunger rod to translate to the second translational configuration when the plunger rod is disposed in the second rotational configuration. A needle is movable relative to the housing from a stowed configuration to a deployed configuration. The needle is moved from the stowed configuration to the deployed configuration by the plunger rod when the plunger rod moves from the first translational configuration to the second translational configuration. A therapeutic agent delivery assembly carries a therapeutic agent and is in communication with the needle. The therapeutic agent delivery assembly is actuated by rotation of the drive wheel relative to the housing and thereby delivers the therapeutic agent to the needle.

According to another exemplary embodiment of the present disclosure, a therapeutic agent delivery system includes a housing. A drive wheel is carried by the housing, and the drive wheel is rotatable relative to the housing from a first rotational configuration to a second rotational configuration. A plunger rod is rotatable with the drive wheel relative to the housing from the first rotational configuration to the second rotational configuration. The plunger rod is translatable relative to the housing from a first translational configuration to a second translational configuration. A plunger restraint maintains the plunger rod in the first translational configuration when the plunger rod is disposed in the first rotational configuration, and the plunger restraint permits the plunger rod to translate to the second translational configuration when the plunger rod is disposed in the second rotational configuration. A needle is movable relative to the housing from a stowed configuration to a deployed configuration and from the deployed configuration to a withdrawn configuration. The needle is moved from the stowed configuration to the deployed configuration by the plunger rod when the plunger rod moves from the first translational configuration to the second translational configuration. A therapeutic agent delivery assembly carries a therapeutic agent and is in fluid communication with the needle. A retraction mechanism is translatable relative to the housing from a third translational configuration to a fourth translational configuration. The retraction mechanism moves the needle from the deployed configuration to the withdrawn configuration when moving from the third translational configuration to the fourth translational configuration.

According to yet another embodiment of the present disclosure, a therapeutic agent delivery system includes a housing. A needle is carried by the housing. A therapeutic agent delivery assembly carries a therapeutic agent and is in fluid communication with the needle. A drive wheel is carried by the housing. The drive wheel is rotatable to: a first rotational configuration in which the needle is in a stowed configuration relative to the housing; a second rotational configuration in which the needle is in a deployed configuration relative to the housing; a third rotational configuration in which the therapeutic agent delivery assembly delivers the therapeutic agent to the needle; and a fourth rotational configuration in which the needle is in a withdrawn configuration relative to the housing.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure relates to systems, devices, and processes for parenteral delivery of therapeutic agents, such as high-viscosity therapeutic fluids. Such systems and devices are illustratively provided with relatively compact and non-linear profiles.

1. Drugs/Therapeutic Agents

Systems and devices according to the present disclosure may carry and facilitate delivery of a drug to a subject. The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by devices according to the present disclosure. The drug may be formulated with one or more excipients. Devices according to the present disclosure are operated in a manner generally as described herein by a patient, caregiver or healthcare professional to deliver a drug to a subject.

In certain embodiments, a therapeutic agent is protein, such as a monoclonal antibody or some other protein which is therapeutically useful. In some embodiments, the protein may have a concentration of from about 75 mg/mL to about 500 mg/mL in a fluid. In certain embodiments, the protein may have a concentration of about 150 mg/mL, 200 mg/mL, 250 mg/mL, or more. A drug may further contain a solvent or non-solvent, such as water, perfluoroalkane solvent, safflower oil, or benzyl benzoate.

A drug may be a fluid, more specifically a high-viscosity fluid and may have an absolute viscosity of from about 5 cP to about 1000 cP. In certain embodiments, a high-viscosity fluid has an absolute viscosity of at least about 10 cP, 20 cP, 30 cP, 40 cP, 50 cP, 60 cP, or more.

2. Therapeutic Agent Delivery System

Figure 2:
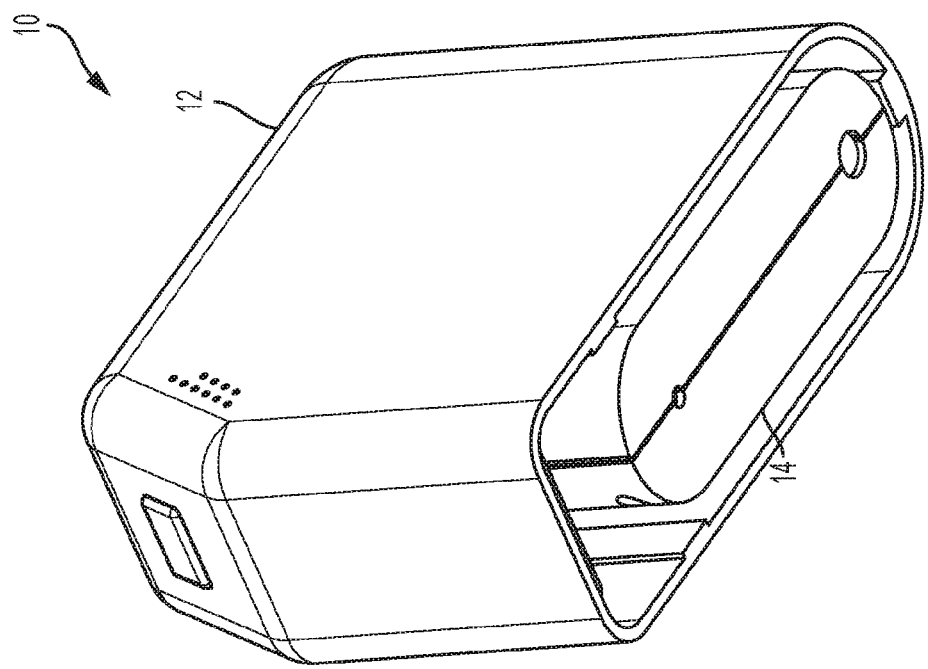
FIG. 2 is a bottom perspective view of the therapeutic agent delivery system of FIG. 1.
Figure 1:
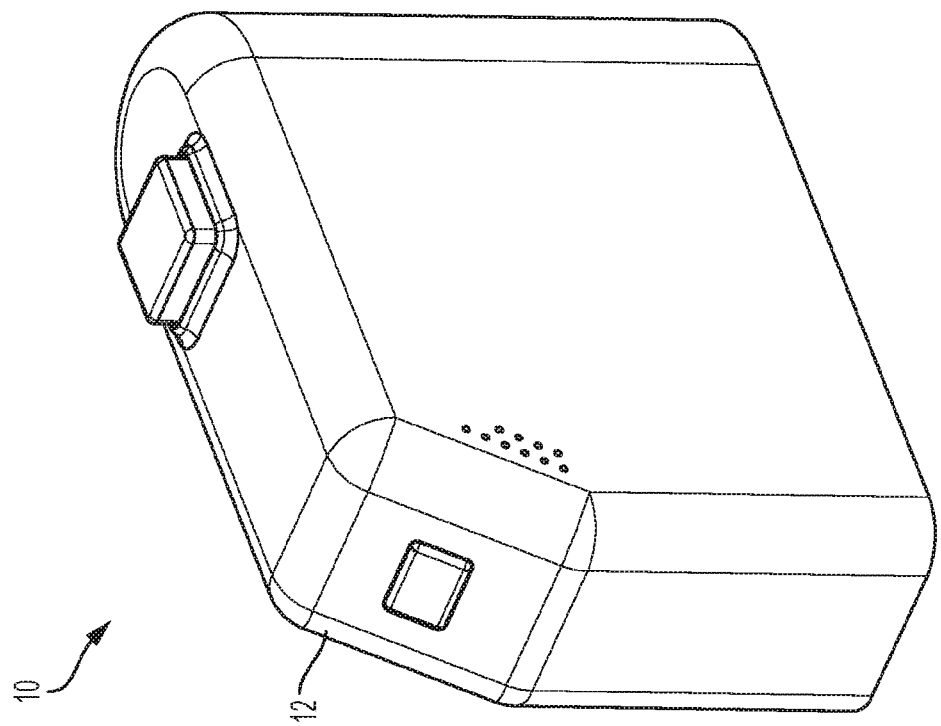
FIG. 1 is a top perspective view of a therapeutic agent delivery system according to an embodiment of the present disclosure.
Figure 3:
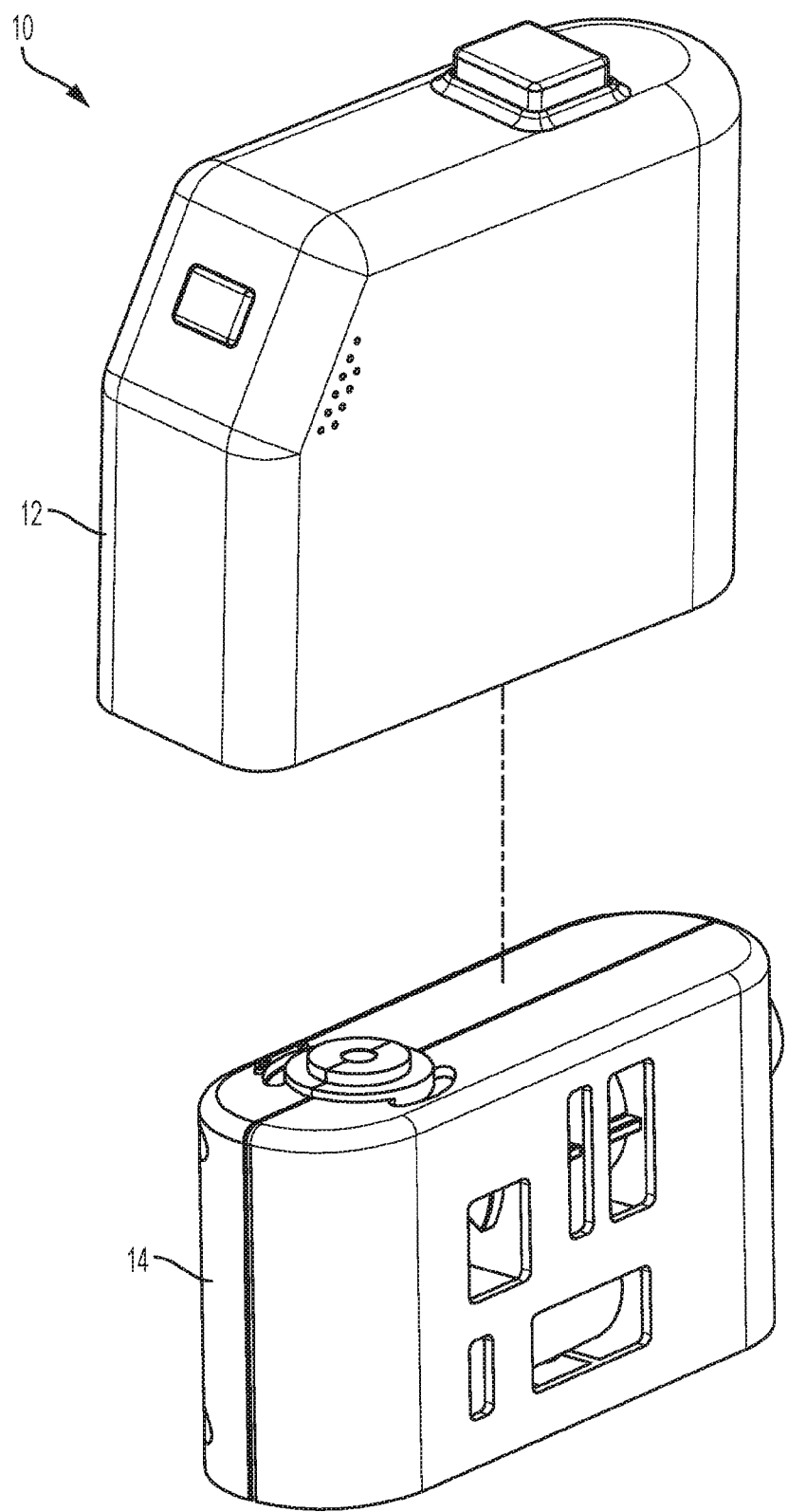
FIG. 3 is a top perspective view of the therapeutic agent delivery system of FIG. 1 with a therapeutic agent delivery device detached from a base device.
Figure 4:
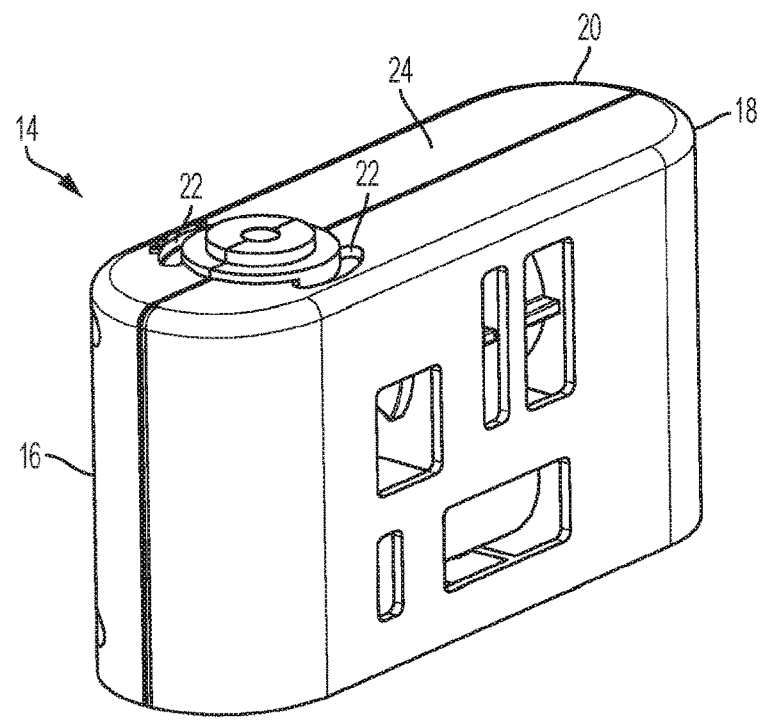
FIG. 4 is a top perspective view of the therapeutic agent delivery device of the therapeutic agent delivery system of FIG. 1.
Figure 5:
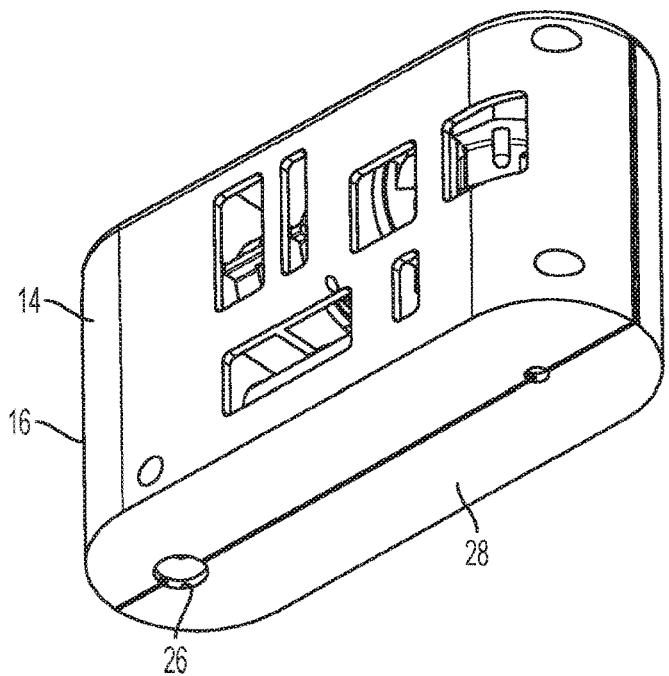
FIG. 5 is a bottom perspective view of the therapeutic agent delivery device of FIG. 4.
Figure 6:
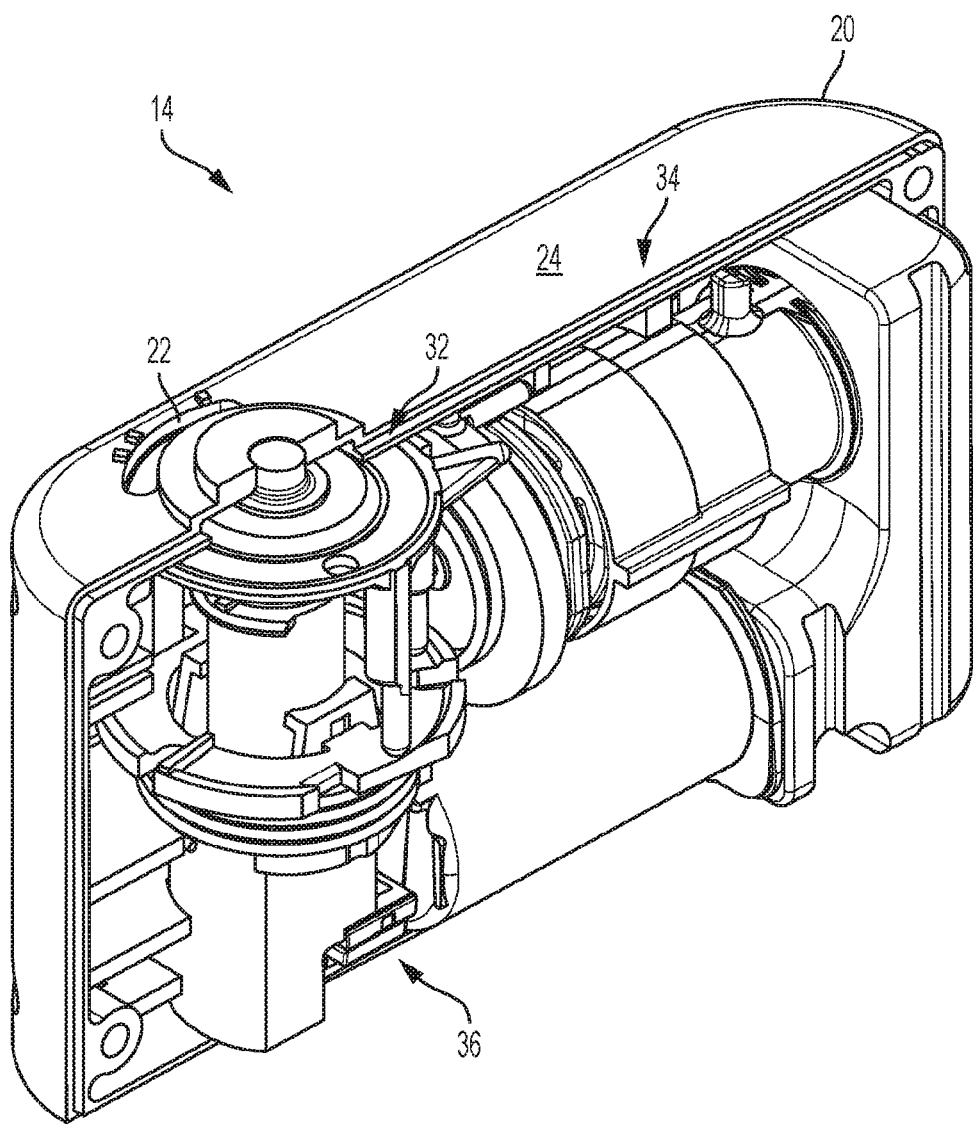
FIG. 6 is a top perspective view of the therapeutic agent delivery device of FIG. 4; a portion of a housing is hidden to illustrate internal components.
Figure 7:
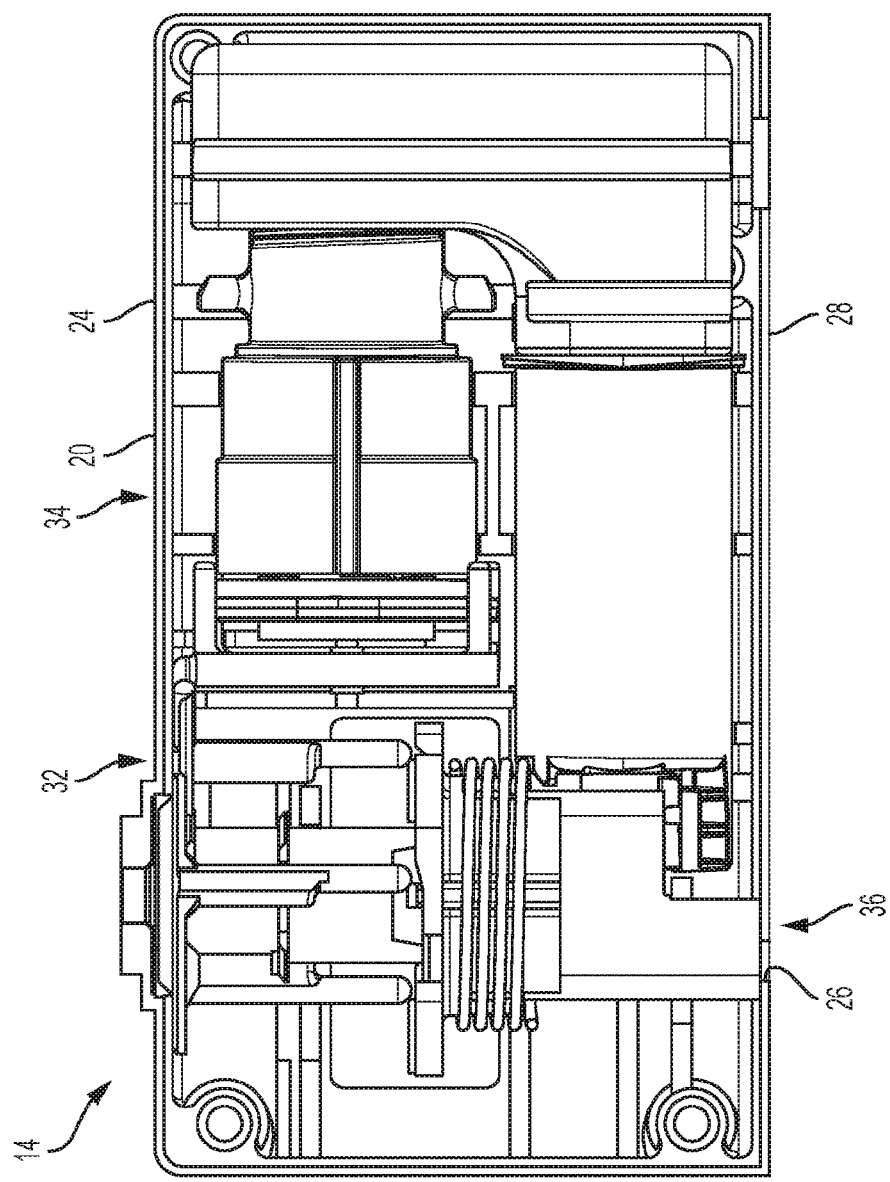
FIG. 7 is a side view of the therapeutic agent delivery device of FIG. 4; a portion of the housing is hidden to illustrate internal components.
Figure 8:
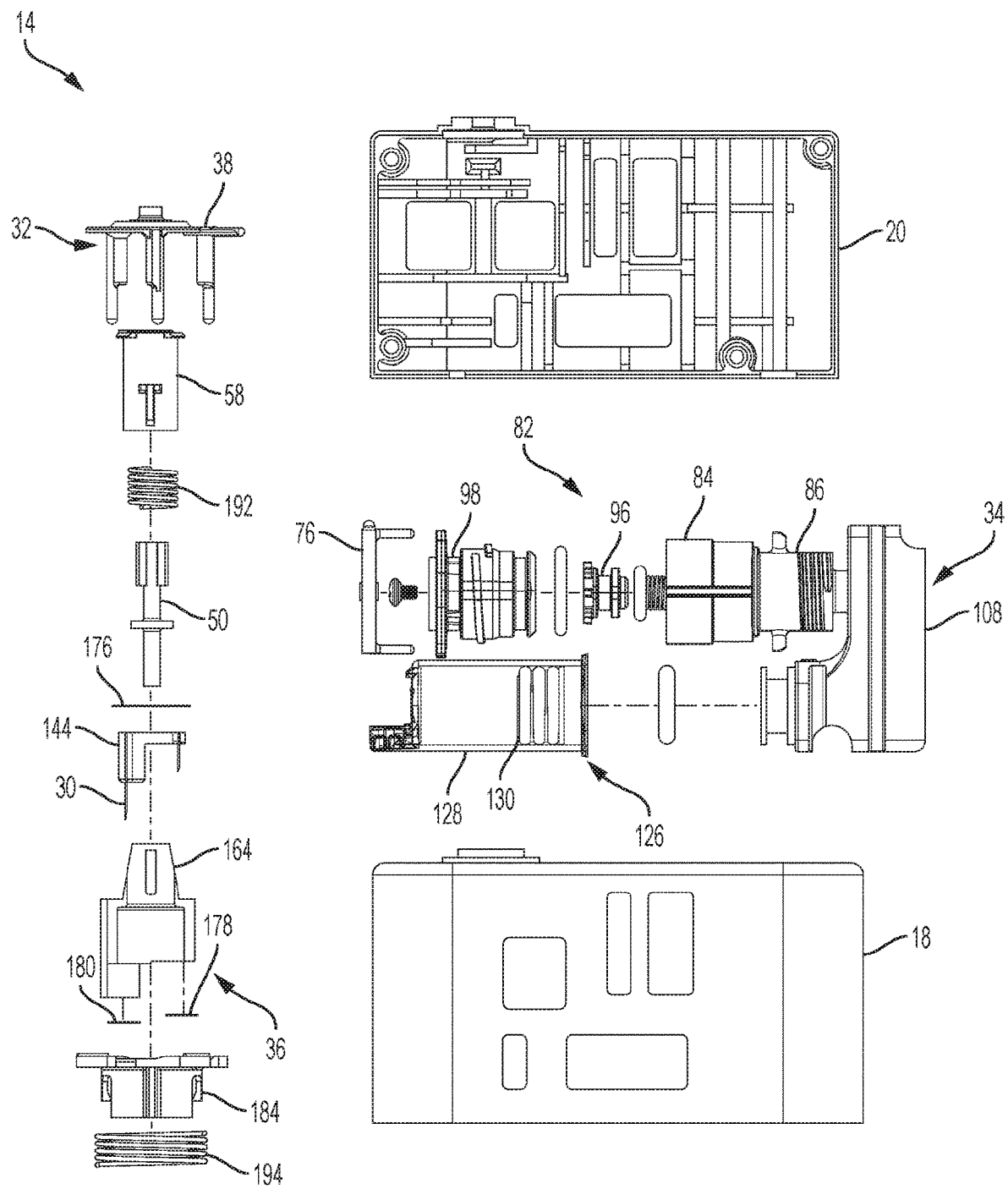
FIG. 8 is an exploded view of the therapeutic agent delivery device of FIG. 4.

FIGS. 1-3 illustrate a therapeutic agent delivery system 10 according to an embodiment of the present disclosure. The system 10 generally includes a user-operable base device 12 that receives a detachable and replaceable therapeutic agent delivery device 14. A user (for example, a patient, a caregiver, or the like) actuates the base device 12, the base device 12 actuates the therapeutic agent delivery device 14, and the therapeutic agent delivery device 14 thereby delivers a therapeutic agent to a subject (for example, a patient). In some embodiments, the therapeutic agent delivery device 14 may then be detached from the base device 12 and discarded (accordingly, the therapeutic agent delivery device 14 may be referred to as a disposable device or a single-use device). Features and components of the therapeutic agent delivery device 14 and the base device 12 are described in further detail below.

A. Therapeutic Agent Delivery Device

FIGS. 4-8 illustrate the therapeutic agent delivery device 14. The therapeutic agent delivery device 14 includes a housing 16 that carries various internal components. The housing 16 illustratively includes a first, or front, portion 18 and a second, or rear, portion 20. In other embodiments, different arrangements are possible. For example, in some embodiments the housing 16 may have additional portions, different first and second portions, or a monolithic structure. The housing 16 includes apertures (illustratively, two arcuate apertures 22 extending through an upper surface 24 of the housing 16) through which the base device 12 engages and actuates internal components of the therapeutic agent delivery device 14. The housing 16 also includes an aperture 26 (illustratively, extending through a lower surface 28 of the housing 16) through which a needle 30 (see FIG. 8) partially extends to deliver the therapeutic agent to the subject.

Referring specifically to FIGS. 5-8, the internal components carried within the housing 16 of the therapeutic agent delivery device 14 are illustrated. The internal components are actuated to facilitate delivery of a therapeutic agent from the therapeutic agent delivery device 14 to the subject. These internal components generally include a deployment mechanism 32 that moves the needle 30 partially outwardly from the housing 16 (that is, to a drug-deployed configuration), a therapeutic agent delivery assembly 34 that initially carries and delivers a therapeutic agent to the needle 30, and a retraction mechanism 36 that moves the needle 30 into the housing 16 after delivering the therapeutic agent to the subject (that is, to a withdrawn configuration). Individual components of the deployment mechanism 32, the therapeutic agent delivery assembly 34, and the retraction mechanism 36 are described in further detail in the following paragraphs, and interaction of the components and operation of the therapeutic agent delivery device 14 are describe in further detail thereafter.

Figure 9:
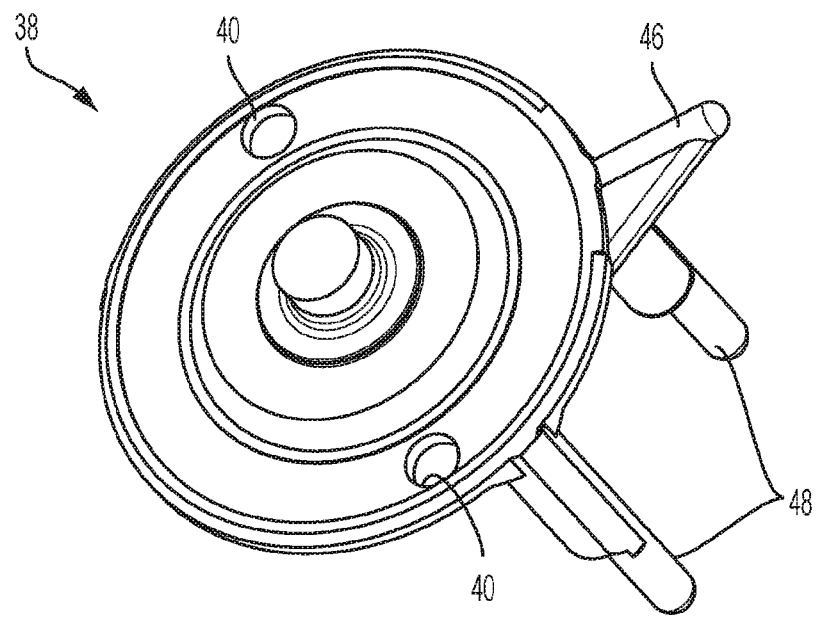
FIG. 9 is a top perspective view of a drive wheel of the therapeutic agent delivery device of FIG. 4.
Figure 10:
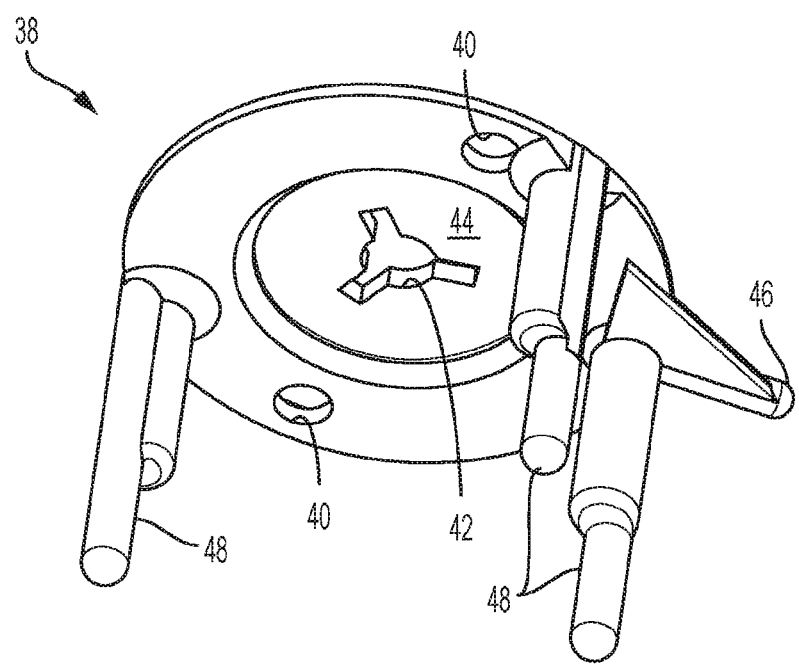
FIG. 10 is a bottom perspective view of the drive wheel of FIG. 9.

FIGS. 9-10 illustrate a rotatable drive wheel 38 of the deployment mechanism 32 of the therapeutic agent delivery device 14. The drive wheel 38 includes one or more coupling features (illustratively, two apertures 40) that facilitate coupling the base device 12 to the drive wheel 38. The drive wheel 38 includes a pocket or recess 42 on a lower surface 44 thereof. As described in further detail below, the recess 42 initially receives another component of the deployment mechanism 32. The drive wheel 38 includes a first actuation feature (illustratively, a radially-outwardly extending arm 46) that engages and drives another component of the deployment mechanism 32 as the drive wheel 38 rotates. The drive wheel 38 further includes a first restraint feature (illustratively, three axially extending arms 48) that inhibit movement of the retraction mechanism 36 relative to the housing 16. In other embodiments, the drive wheel 38 may have different structures. For example, in some embodiments the drive wheel 38 may have different numbers and/or types of coupling features, actuation features, and/or restraint features. More specifically, in some embodiments positive features (for example, the radially-outwardly extending arm 46 and/or the axially extending arms 48) may be replaced with negative features (for example, recesses or apertures).

Figure 12:
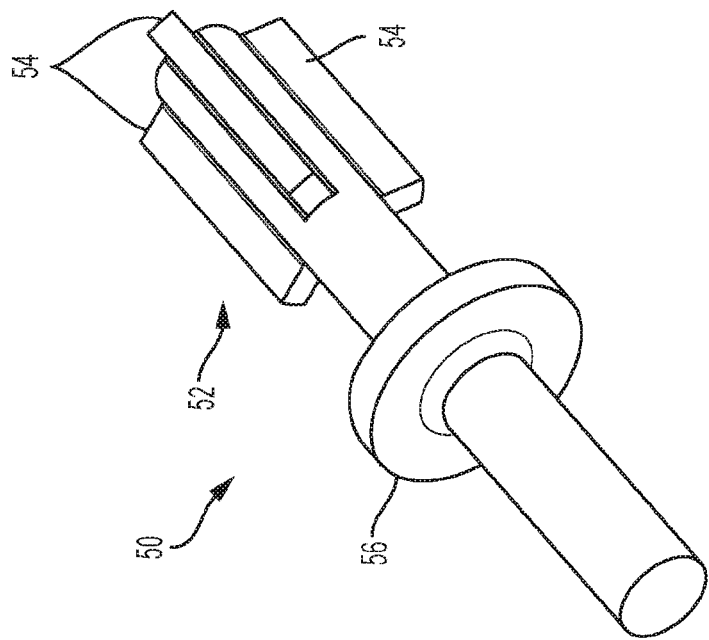
FIG. 12 is a bottom perspective view of the plunger rod of FIG. 11.
Figure 11:
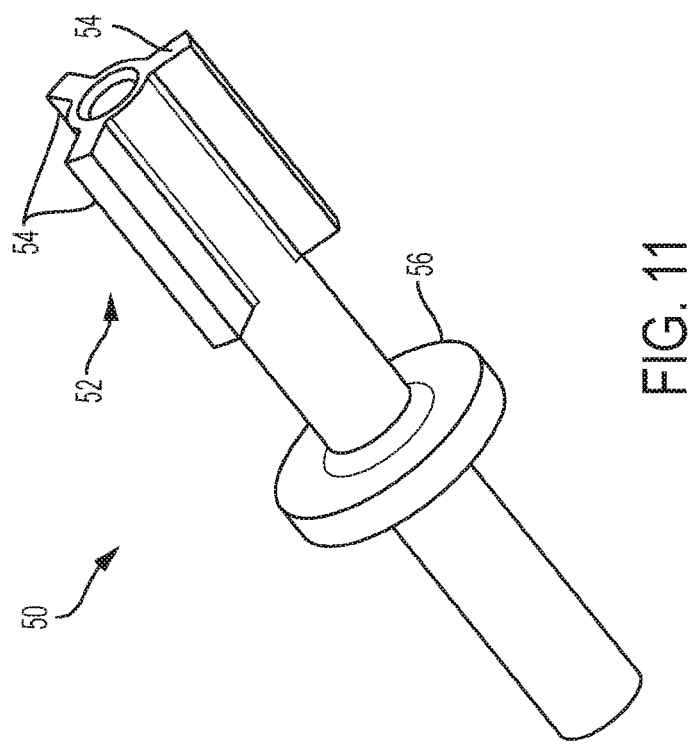
FIG. 11 is a top perspective view of a plunger rod of the therapeutic agent delivery device of FIG. 4.

FIGS. 11-12 illustrate a plunger rod 50 of the deployment mechanism 32 of the therapeutic agent delivery device 14. The plunger rod 50 includes an upper end portion 52 that has a first restraint feature (illustratively, three radially-outwardly extending ribs 54) that, as described in further detail below, inhibit movement of the plunger rod 50 relative to the housing 16. The radially-outwardly extending ribs 54 also provide the upper end portion 52 of the plunger with the same general cross-sectional shape as the recess of the drive wheel 38. Having the same general cross-sectional shapes facilitates initially rotating the plunger rod 50 together with the drive wheel 38. The plunger rod 50 further includes a flange 56 that engages a compression spring (shown elsewhere) to facilitate moving the plunger rod 50 relative to the housing 16. In other embodiments, the plunger rod 50 may have different structures. For example, in some embodiments the plunger rod 50 may have different numbers and/or types of restraint features.

Figure 14:
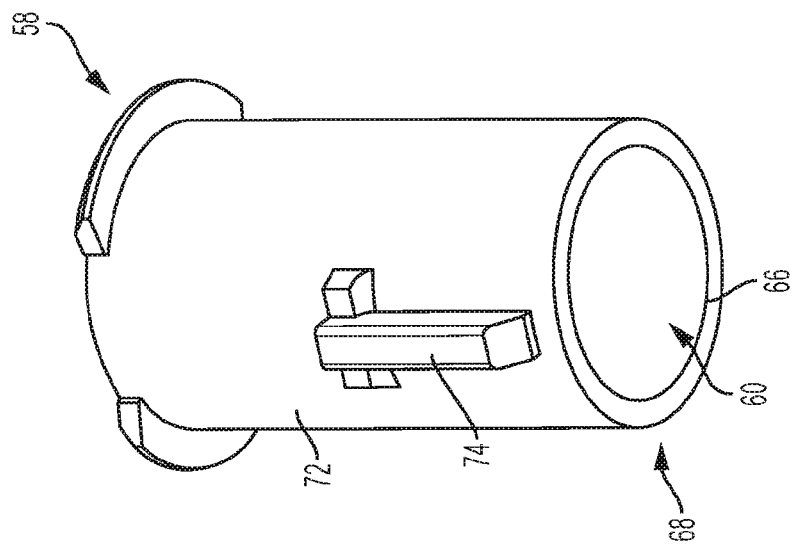
FIG. 14 is a bottom perspective view of the plunger restraint of FIG. 13.
Figure 13:
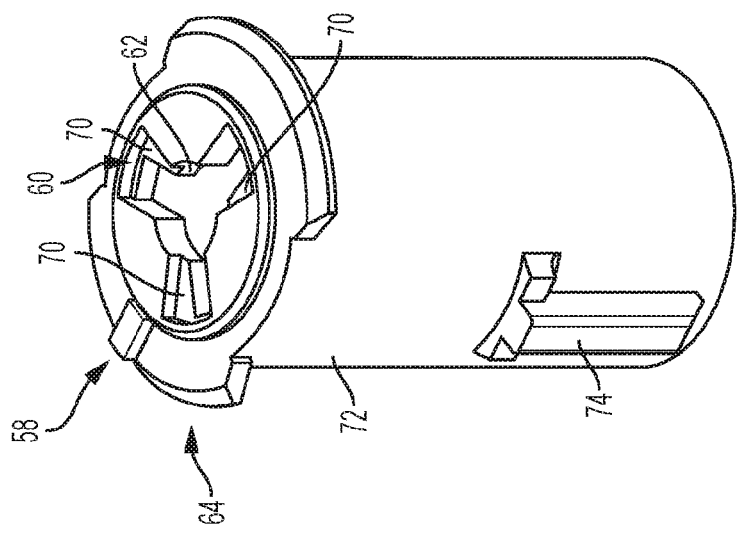
FIG. 13 is a top perspective view of a plunger restraint of the therapeutic agent delivery device of FIG. 4.

FIGS. 13-14 illustrate a plunger restraint 58 of the deployment mechanism 32 of the therapeutic agent delivery device 14. The plunger restraint 58 is a generally hollow, tube-like component that includes an inner passageway 60. The inner passageway 60 extends from a first opening 62 at a first end portion 64 of the plunger restraint 58 to a second opening 66 at a second end portion 68 of the plunger restraint 58. The first end portion 64 of the plunger restraint 58 includes a second restraint feature (illustratively, three stop surfaces 70) that, as described in further detail below, engages the first restraint feature of the plunger rod 50 to inhibit movement of the plunger rod 50 within the housing 16. The first opening 62 of the plunger restraint 58 has the same general cross-sectional shape as the upper end portion 52 of the plunger rod 50. Accordingly, the upper end portion 52 of the plunger rod 50 may extend through the first opening 62 of the plunger restraint 58 when the plunger rod 50 is in appropriate angular alignment with the first opening 62. Between the first end portion 64 and the second end portion 68 of the plunger restraint 58, an outer surface 72 includes a coupling feature (illustratively, two T-shaped protrusions 74, one of which is obscured in FIGS. 13-14) for coupling the plunger restraint 58 to the retraction mechanism 36. In other embodiments, the plunger restraint 58 may have different structures.

Figure 15:
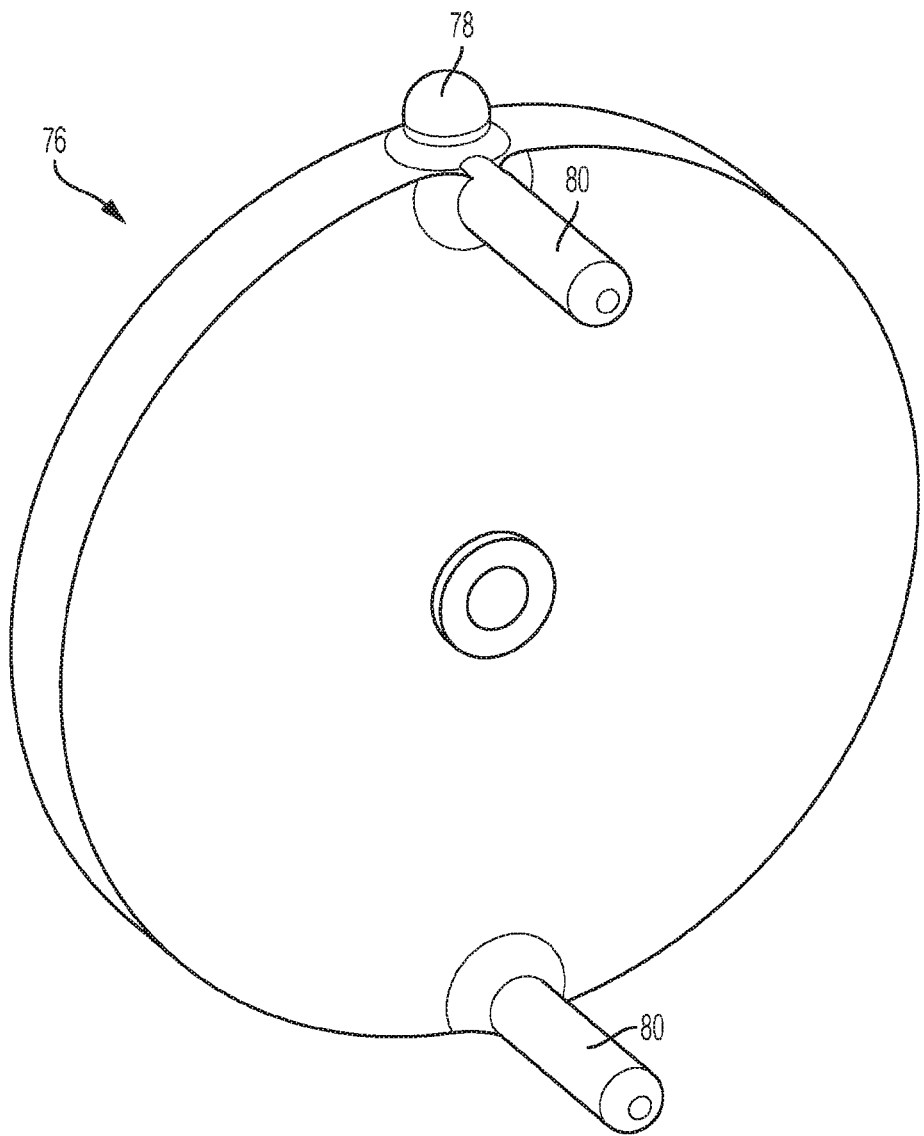
FIG. 15 is a top perspective view of an activation wheel of the therapeutic agent delivery device of FIG. 4.
Figure 16:
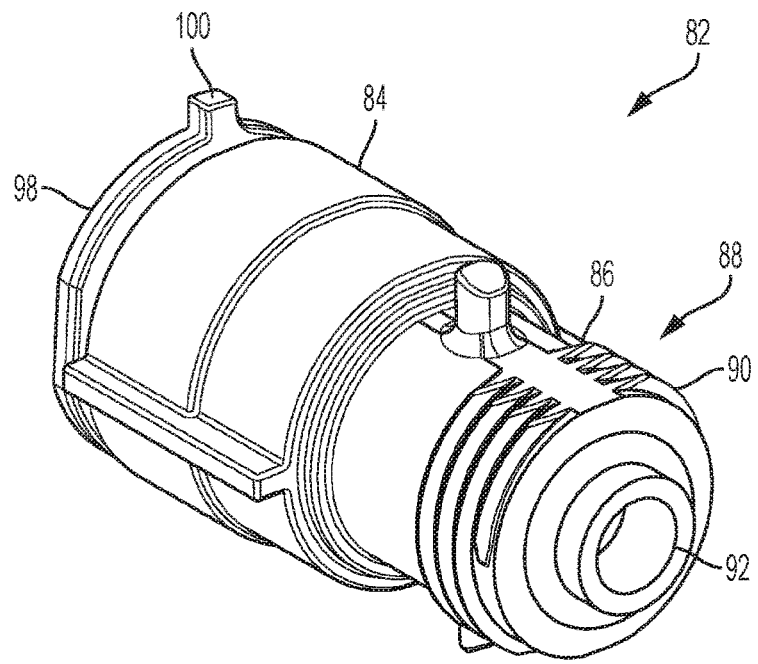
FIG. 16 is a first side perspective view of a pressure generating actuator of the therapeutic agent delivery device of FIG. 4.
Figure 17:
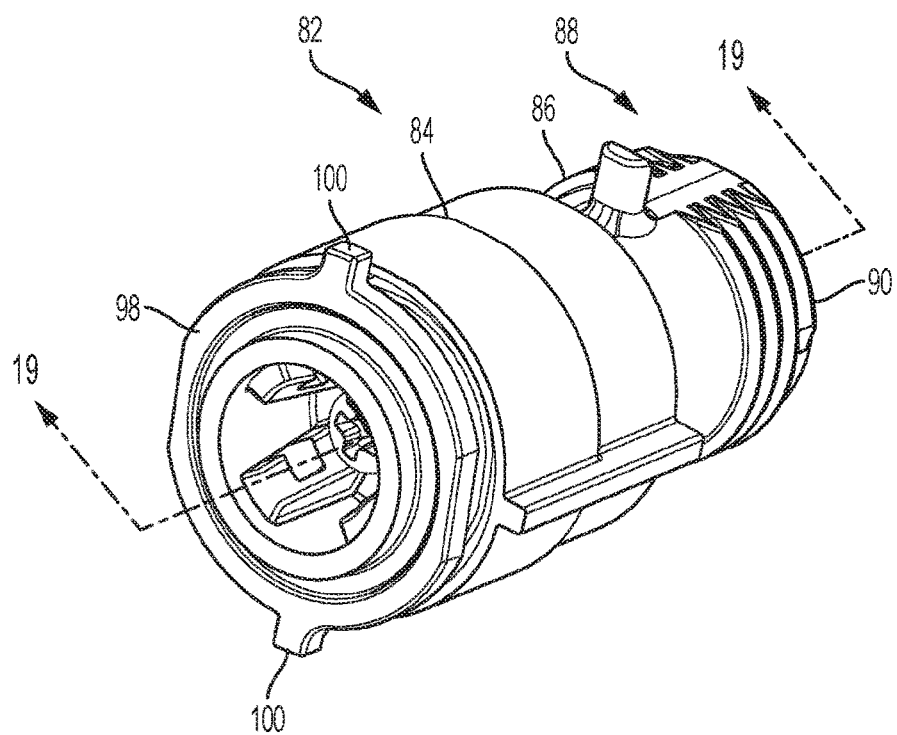
FIG. 17 is a second side perspective view of the pressure generating actuator of FIG. 16.
Figure 18:
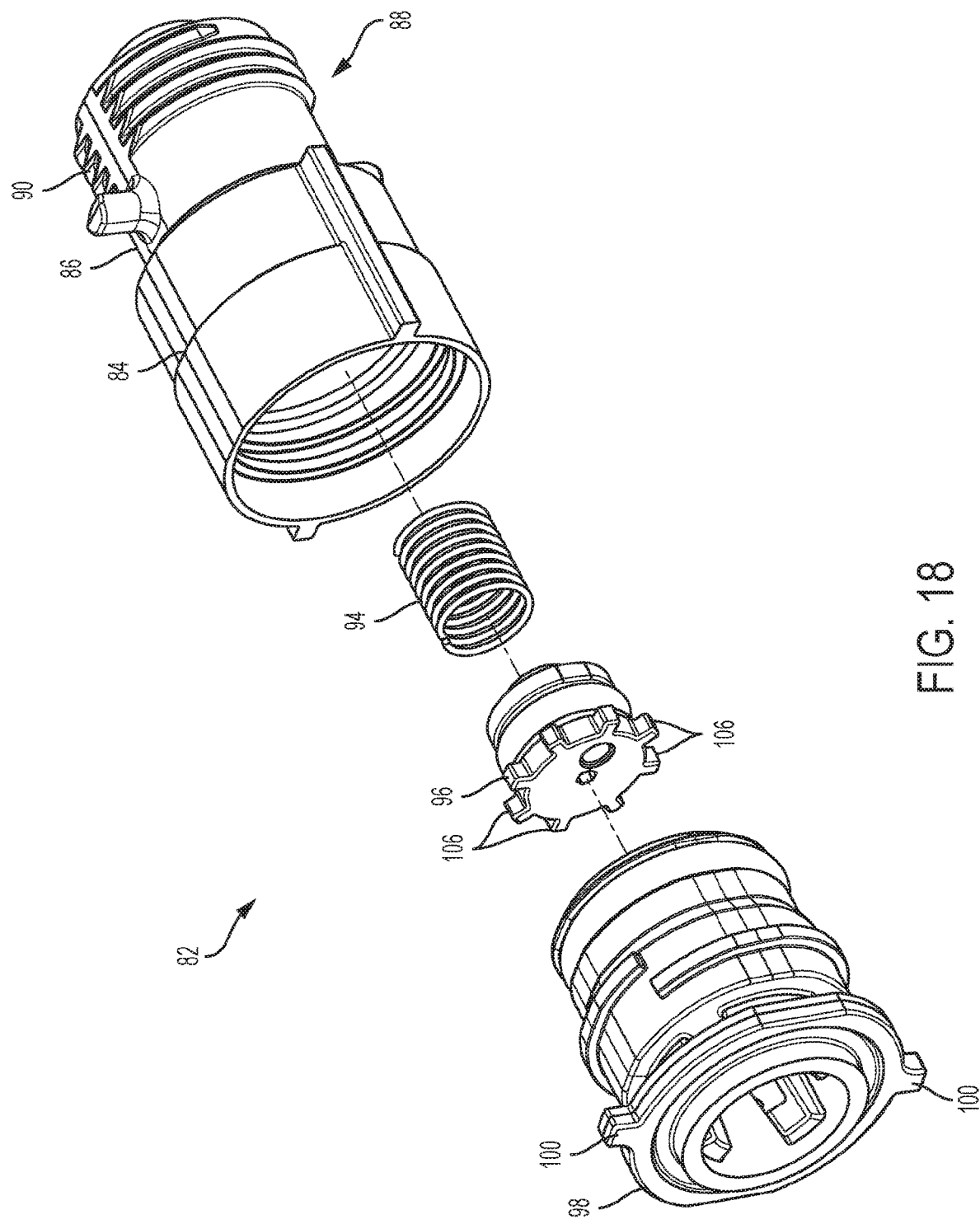
FIG. 18 is an exploded perspective view of the pressure generating actuator of FIG. 16.

FIG. 15 illustrates a rotatable activation wheel 76 of the deployment mechanism 32 of the therapeutic agent delivery device 14. The activation wheel 76 is generally an annular component. The activation wheel 76 includes a second actuation feature (illustratively, a radially-outwardly extending finger 78) that, as described in further detail below, is engaged and driven by the first actuation feature of the drive wheel 38. The activation wheel 76 also includes a shuttle actuation feature (illustratively, two axially extending arms 80) that engage and actuate the therapeutic agent delivery assembly 34. In other embodiments, the activation wheel 76 may have different structures. For example, in some embodiments the activation wheel 76 may have different numbers and/or types of actuation features. More specifically, in some embodiments the actuation features may be negative features (for example, recesses or apertures) instead of positive features.

FIGS. 16-19 illustrate a pressure generating actuator 82 of the therapeutic agent delivery assembly 34. Generally, the pressure generating actuator 82 is actuated by the deployment mechanism 32 to facilitate mixing of internally-carried chemical reagents, which generates one or more pressurized fluids (for example, one or more gases). Examples of suitable reagents and generated gases are provided below. As described in further detail below, the pressurized fluid(s) are delivered to and facilitate movement of other components of the therapeutic agent delivery assembly 34.

The pressure generating actuator 82 includes a first mixing chamber 84 and a second mixing chamber 86, which are illustratively monolithically formed with each other. At an outlet end portion 88, the mixing chambers 84, 86 include an outlet coupling feature (illustratively, an externally threaded surface 90) for coupling to another component of the therapeutic agent delivery assembly 34. The outlet end portion 88 also includes an actuator outlet 92 through which pressurized fluid is discharged from the pressure generating actuator 82. The mixing chambers 84, 86 carry an actuator spring 94, a mixing piston 96, and a rotatable shuttle 98 in a longitudinally stacked arrangement.

Figure 19:
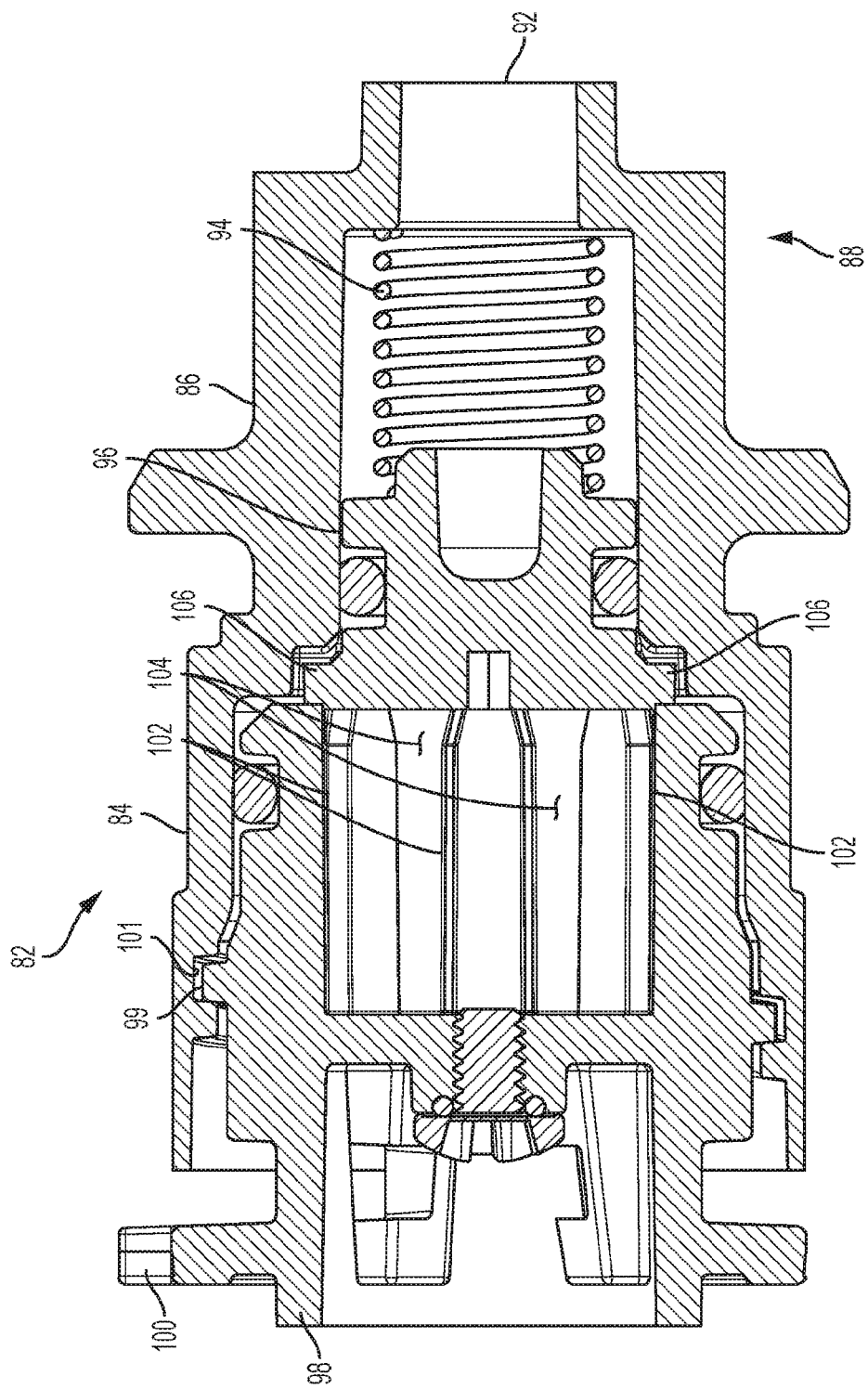
FIG. 19 is a longitudinal sectional view of the pressure generating actuator along line 19-19 of FIG. 17.

The first mixing chamber 84 and the shuttle 98 form a helical coupling for movably coupling to each other. Illustratively, the shuttle 98 includes a helically extending ridge 99 and the first mixing chamber 84 includes a helically extending groove 101 that receives the ridge 99. The shuttle 98 includes an actuation feature (illustratively, two radially-outwardly extending fingers 100) that engage and are driven by the shuttle actuation feature of the activation wheel 76 (illustratively, the two axially extending arms 80). Internally, the shuttle 98 includes a first restraining feature (illustratively, eight radially-inwardly extending tabs 102) that engages the mixing piston 96. Illustratively, the shuttle 98 also includes channels 104 disposed between adjacent tabs 102. The mixing piston 96 includes a second restraining feature (illustratively, eight radially-outwardly extending tabs 106) that engages the first restraining feature of the shuttle 98. In an initial configuration, as shown in FIG. 19, the first restraining feature engages the second restraining feature (illustratively, the radially-inwardly extending tabs 102 of the shuttle 98 are angularly aligned with and engage the radially-outwardly extending tabs 106 of the mixing piston 96) to hold the mixing piston 96 in a position between the first mixing chamber 84 and the second mixing chamber 86. The mixing piston 96 thereby maintains separation of reagents in the first mixing chamber 84 and the second mixing chamber 86. In the initial configuration, the actuator spring 94 is also compressed within the second mixing chamber 86 against the mixing piston 96. In a subsequent configuration, as described in further detail below, the shuttle 98 rotates relative to the first mixing chamber 84 and the second mixing chamber 86 to disengage the first restraining feature from the second restraining feature (illustratively, the radially-inwardly extending tabs 102 of the shuttle 98 are angularly misaligned with, or angularly offset from, the radially-outwardly extending tabs 106 of the mixing piston 96, and the channels 104 are angularly aligned with the radially-outwardly extending tabs 106 of the mixing piston 96). As a result, the actuator spring 94 expands and moves the mixing piston 96 into the shuttle 98 and the first mixing chamber 84, which permits the reagents in the first mixing chamber 84 and the second mixing chamber 86 to mix. Mixing of the reagents generates one or more pressurized fluids (for example, one or more gases), and the pressurized fluid(s) are delivered to and facilitate movement of other components of the therapeutic agent delivery assembly 34.

In some embodiments, pressure generating actuators have different structures. For example, suitable pressure generating actuators include those described in: U.S. Pat. No. 9,795,740 titled "Chemical Engines and Methods for Their Use, Especially in the Injection of Highly Viscous Fluids"; International PCT Application No. PCT/US2018/017547, titled "Processes and Devices for Delivery of Fluid by Chemical Reaction" and filed Feb. 9, 2018; and International PCT Application No. PCT/US2018/049048, titled "System for Controlling Gas Generation with a Drug Delivery Device" and filed on Aug. 31, 2018, the disclosures of which are expressly incorporated herein by reference in their entirety.

Any suitable chemical reagent or reagents can be used to generate one or more pressurized fluids in pressure generating actuators of the present disclosure. Examples of generated gases include carbon dioxide gas, nitrogen gas, oxygen gas, chlorine gas, etc. Desirably, the generated gas is inert and non-flammable. The amount of gas needed to facilitate movement of other components of the therapeutic agent delivery assembly may impact the type, amount, and concentration of each reagent used in pressure generating actuators. The reagents may be in dry form (for example, powdered form, tablet form) and/or in liquid form.

In one exemplary embodiment, a bicarbonate (which may be present in dry form) reacts with an acid (which may be present in liquid form) to produce carbon dioxide gas in pressure generating actuators. Examples of suitable bicarbonates include sodium bicarbonate, potassium bicarbonate, and ammonium bicarbonate. Other ingredients may also be present along with the bicarbonates, such as diatomaceous earth. Examples of suitable acids include acetic acid, citric acid, potassium bitartrate, disodium pyrophosphate, and calcium dihydrogen phosphate. In one particular example, the bicarbonate is potassium bicarbonate and the acid is aqueous citric acid, which may react to produce carbon dioxide gas and a liquid mixture of water and dissolved potassium citrate.

In some embodiments, other reactions may be used. In one example, a metal carbonate, such as copper carbonate or calcium carbonate, is thermally decomposed to produce carbon dioxide gas and the corresponding metal oxide in pressure generating actuators. In another example, 2,2'-azobisisobutyronitrile (AIBN) is heated to produce nitrogen gas in pressure generating actuators. In yet another example, enzymes (for example yeast) are reacted with sugar to produce carbon dioxide gas in pressure generating actuators. Some substances readily sublime, going from solid to gas. Such substances include but are not limited to naphthalene and iodine. In still yet another example, hydrogen peroxide is decomposed with catalysts such as enzymes (for example catalase) or manganese dioxide to produce oxygen gas in pressure generating actuators. In still yet another example, silver chloride is decomposed through exposure to light to generate a gas in pressure generating actuators. Suitable reagents, chemical formulations, and reactions used to drive the therapeutic agent delivery assembly of the present disclosure are further described in the above-incorporated U.S. Pat. No. 9,795,740, International PCT Application No. PCT/US2018/017547, and International PCT Application No. PCT/US2018/049048.

Figure 21:
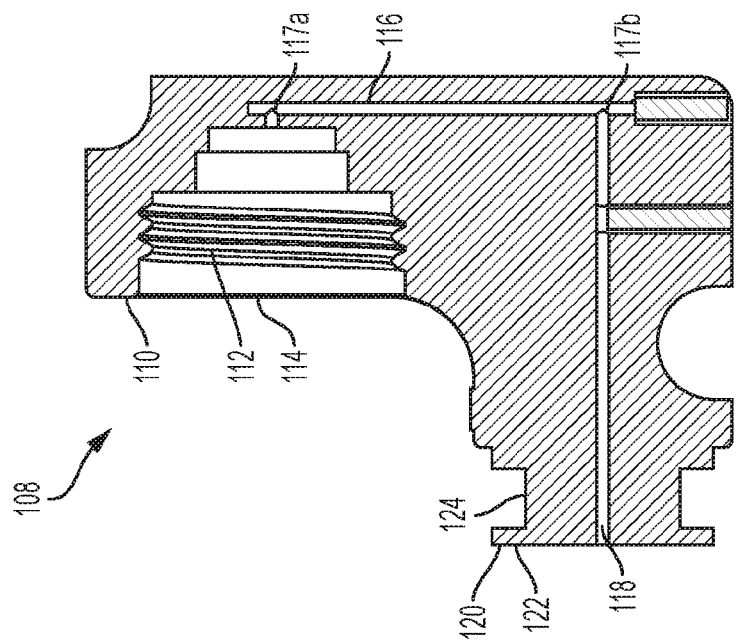
FIG. 21 is a side sectional view of the pressurized fluid manifold along line 21-21 of FIG. 20.
Figure 20:
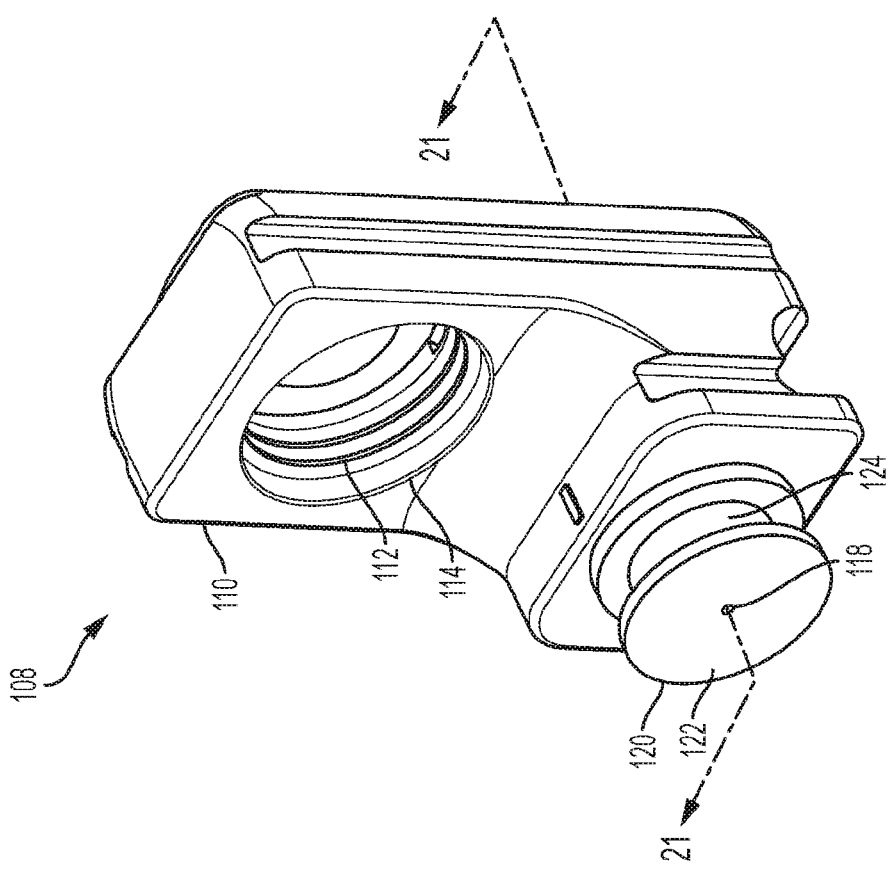
FIG. 20 is a top perspective view of a pressurized fluid manifold of the therapeutic agent delivery device of FIG. 4.

FIGS. 20-21 illustrate a pressurized fluid manifold 108 of the therapeutic agent delivery assembly 34. The pressurized fluid manifold 108 includes an manifold inlet portion 110 having an inlet coupling feature for coupling to the outlet coupling feature of the pressure generating actuator 82 (illustratively, an internal threaded surface 112 for coupling to the external threaded surface 90 of the pressure generating actuator 82). The manifold inlet portion 110 also includes a manifold inlet 114 for receiving pressurized fluid from the actuator outlet 92. The manifold inlet 114 is in fluid communication with a manifold passageway 116. Illustratively, the manifold passageway 116 includes two substantially 90 degree turns 117a, 117b (that is, two 90 degree±5 degree turns) and, as a result, is configured to redirect pressurized fluid in substantially the opposite direction (that is, the opposite direction±5 degrees) from which it is received. Opposite the manifold inlet 114, the manifold passageway 116 is in fluid communication with a manifold outlet 118 of a manifold outlet portion 120 of the pressurized fluid manifold 108. The manifold outlet portion 120 also includes an outlet coupling feature for coupling to another component of the therapeutic agent delivery assembly 34 (illustratively, a flange 122 and a recessed circumferential surface 124 for receiving an o-ring (shown elsewhere), the o-ring press-fittingly engaging the other component of the therapeutic agent delivery assembly 34). In other embodiments, the pressurized fluid manifold 108 may have different structures. For example, in some embodiments the manifold passageway 116 has a different number of turns, different types of turns, or may lack turns.

Figure 23:
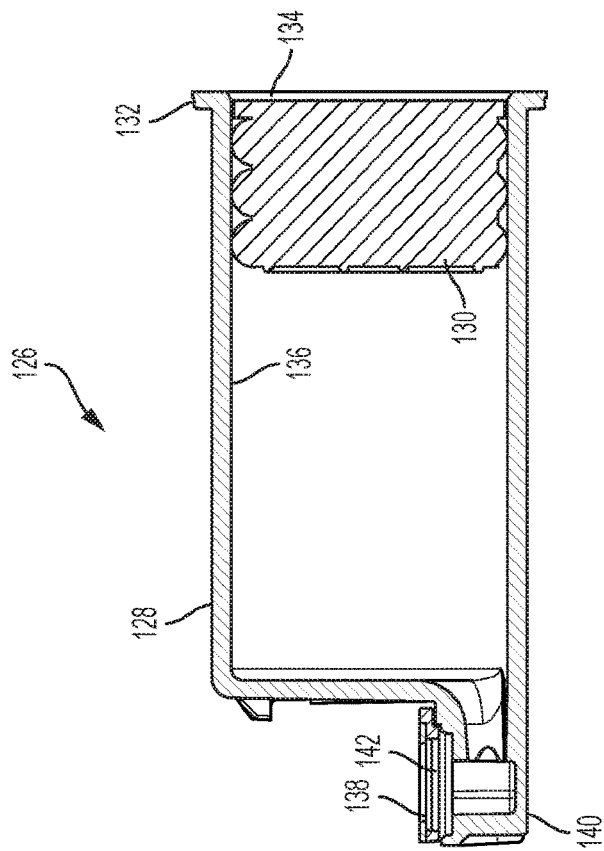
FIG. 23 is a side sectional view of the syringe assembly along line 23-23 of FIG. 22.
Figure 22:
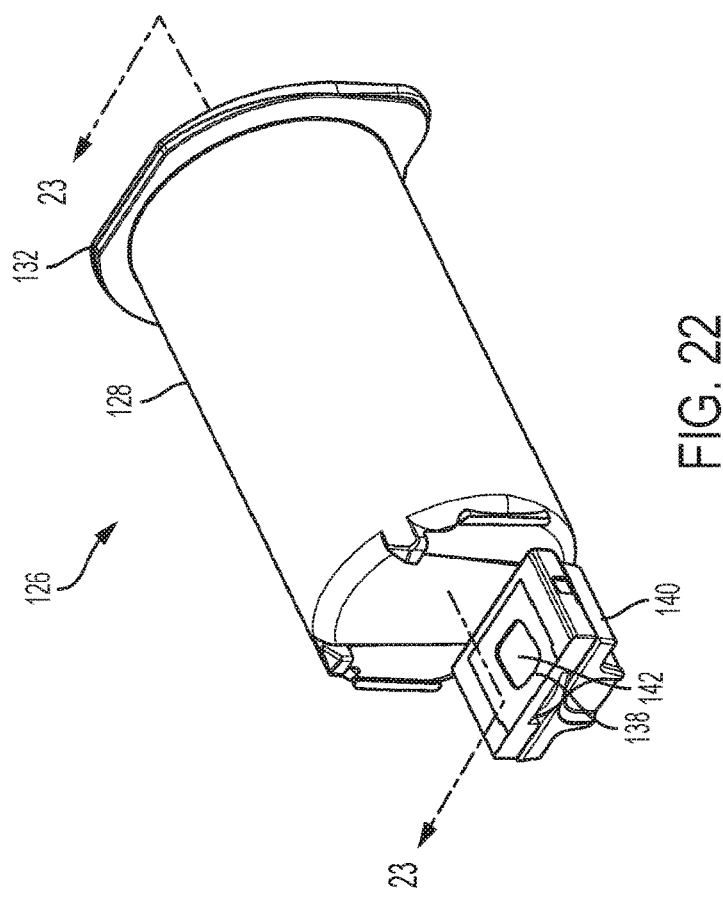
FIG. 22 is a top perspective view of a syringe assembly of the therapeutic agent delivery device of FIG. 4.

FIGS. 22-23 illustrate a syringe assembly 126 of the therapeutic agent delivery assembly 34. The syringe assembly 126 includes a syringe chamber 128 and a syringe piston 130 that is movably carried within the syringe chamber 128. The syringe chamber 128 includes a syringe inlet portion 132 that couples to the outlet coupling feature of the pressurized fluid manifold 108. The syringe inlet portion 132 includes a syringe inlet 134 for receiving pressurized fluid from the manifold outlet 118. The syringe inlet 134 is in fluid communication with a syringe passageway 136, in which the syringe piston 130 is movably disposed. The syringe passageway 136 carries a therapeutic agent on the opposite side of the piston relative to the syringe inlet 134. The syringe passageway 136 is illustratively sized to carry 2.25 mL of the therapeutic agent. In other embodiments, the syringe passageway 136 is sized to carry other volumes of the therapeutic agent, including, for example, 5 mL, 10 mL, or any other suitable volume. Opposite the syringe inlet 134, the syringe passageway 136 is in fluid communication with a syringe outlet 138 of a syringe outlet portion 140. Illustratively, the syringe outlet 138 is disposed substantially perpendicularly relative to the syringe inlet 134 (that is, perpendicular±5 degrees). In other embodiments, the syringe outlet 138 is disposed non-perpendicularly relative to the syringe inlet 134. The syringe outlet portion 140 further includes a pierceable seal (illustratively, a foil strip 142) that covers the syringe outlet 138. In other embodiments, other arrangements are possible. For example, the syringe assembly 126 could be replaced by another type of therapeutic agent container, such as a bellows or bladder structure.

Figure 25:
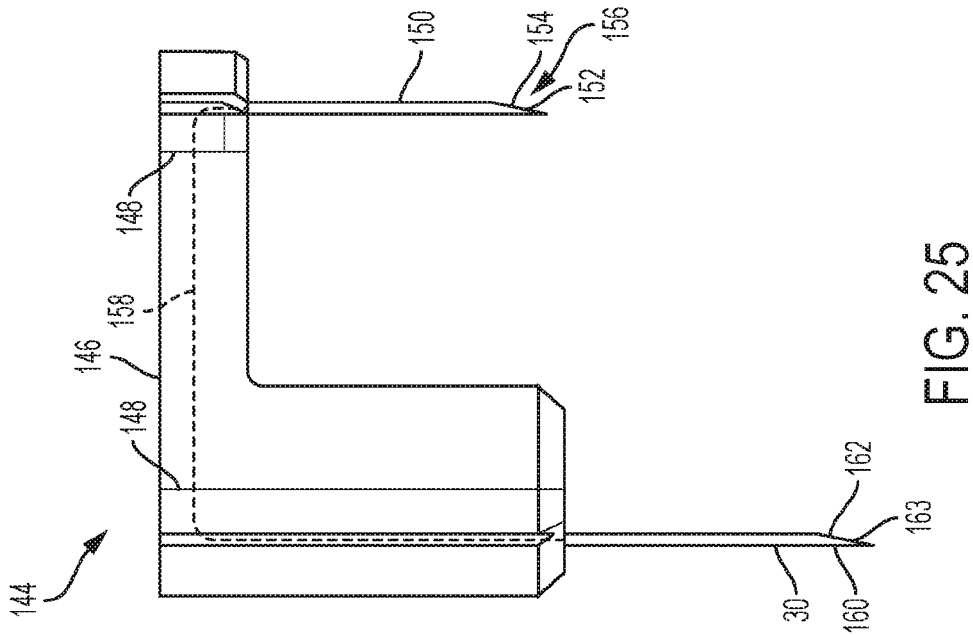
FIG. 25 is a side view of the needle assembly of FIG. 24.
Figure 24:
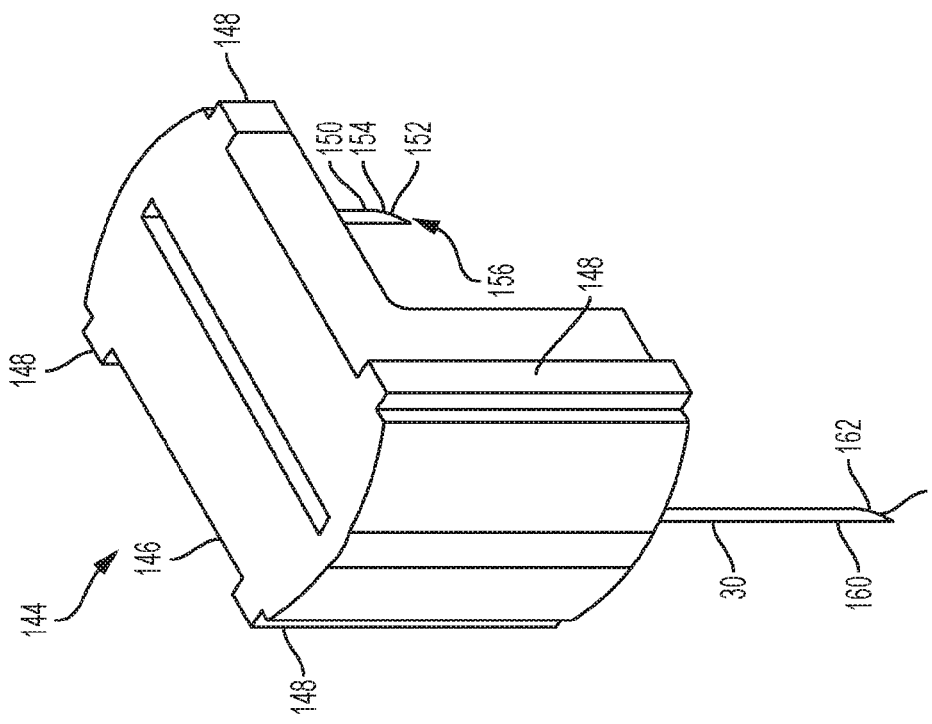
FIG. 24 is a top perspective view of a needle assembly of the therapeutic agent delivery device of FIG. 4.

FIGS. 24-25 illustrate a needle assembly 144 of the therapeutic agent delivery assembly 34. The needle assembly 144 includes a needle carrier 146, which carries the needle 30. The needle carrier 146 includes a guide feature (illustratively, four guide rails 148) that facilitates translation of the needle assembly 144. The needle 30 includes a needle inlet portion 150. The needle inlet portion 150 includes a first piercing tip 152 that is configured to pierce the pierceable seal of the syringe outlet portion 140. The needle inlet portion 150 also includes a needle inlet 154 for receiving the therapeutic agent from the syringe outlet 138. The needle inlet 154 is in fluid communication with a needle passageway 156, which extends from the needle inlet 154, through the needle inlet portion 150, through a connection portion 158, and through a needle outlet portion 160. At the needle outlet portion 160, the needle passageway 156 is in fluid communication with a needle outlet 162 through which the needle 30, and the therapeutic agent delivery device 14, discharge the therapeutic agent. The needle outlet portion 160 also includes a second piercing tip 163 that is configured to pierce the skin of the subject. Illustratively, the needle outlet portion 160 and the needle inlet portion 150 are disposed substantially perpendicularly relative to the connection portion 158 (that is, perpendicular±5 degrees). Stated another way, the needle 30 may be a "J-needle" 30. In other embodiments, the needle assembly 144 may have different structures. For example, the needle outlet portion 160 and/or the needle inlet portion 150 may be disposed non-perpendicularly relative to the connection portion 158. Another specific example of a needle assembly 144 having a different structure is provided below.

Figure 28:
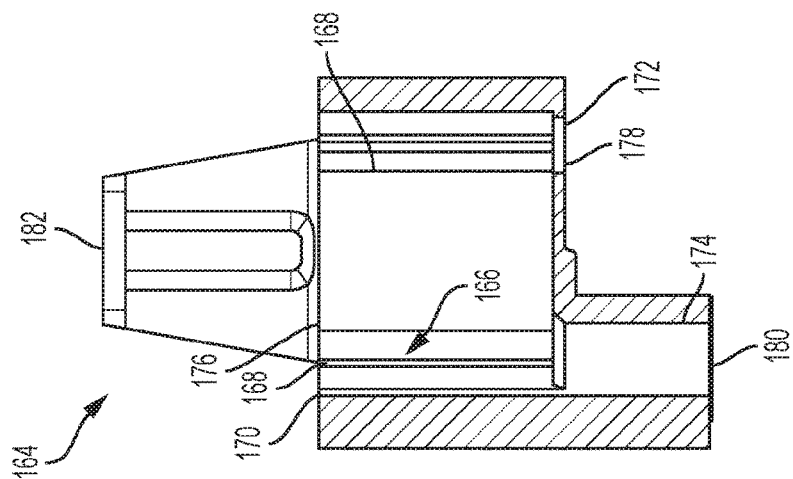
FIG. 28 is a side sectional view of the needle assembly container along line 28-28 of FIG. 26.
Figure 27:
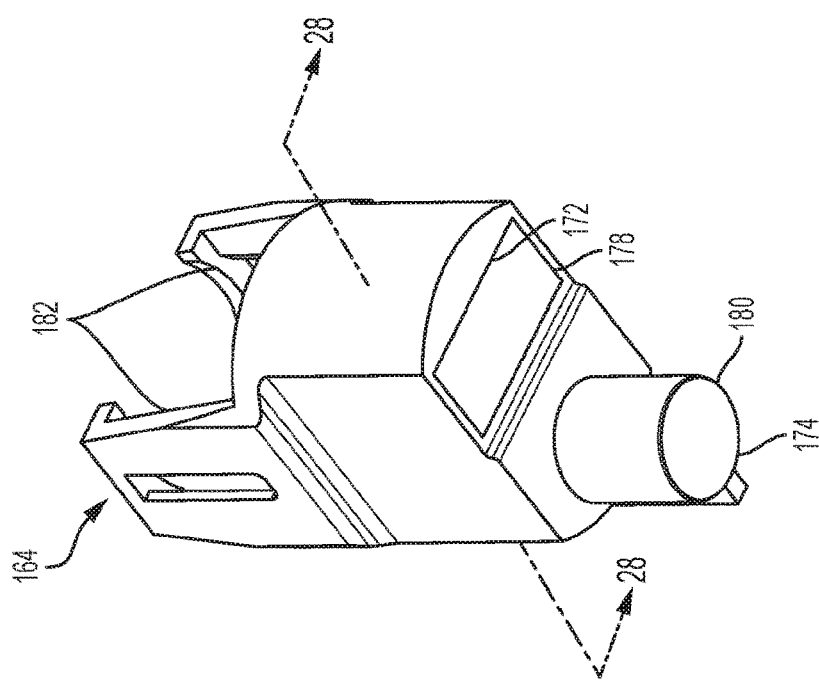
FIG. 27 is a bottom perspective view of the needle assembly container of FIG. 26.
Figure 26:
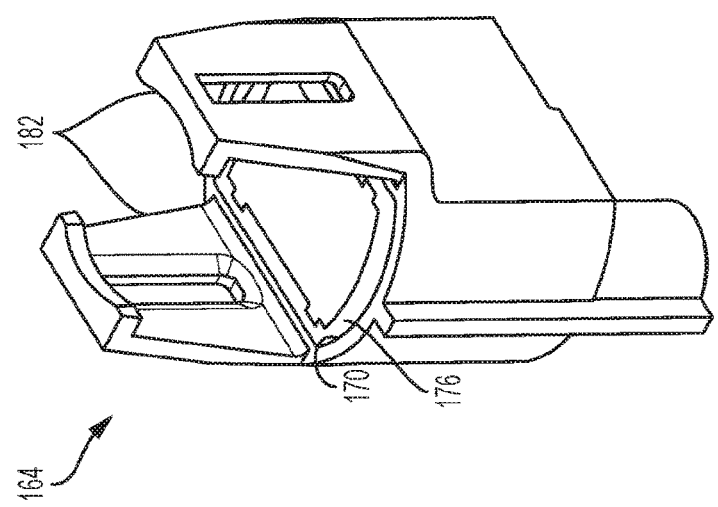
FIG. 26 is a top perspective view of a needle assembly container of the therapeutic agent delivery device of FIG. 4.

FIGS. 26-28 illustrate a needle assembly container 164 of the retraction mechanism 36. The needle assembly container 164 includes an inner cavity 166 that carries the needle assembly 144. The inner cavity 166 includes an internal guide feature (illustratively, four guide channels 168, two of which are shown in FIG. 28) that couples to the guide feature of the needle assembly 144 (illustratively, the guide rails 148) to facilitate translation of the needle assembly 144 within the inner cavity 166. The inner cavity 166 also includes an upper opening 170, through which the plunger rod 50 is configured to extend, a first lower opening 172, through which the needle inlet portion 150 is configured to extend, and a second lower opening 174, through which the needle outlet portion 160 is configured to extend. The needle assembly container 164 includes a first pierceable seal (illustratively, a foil strip 176), a second pierceable seal (illustratively, a foil strip 178), and a third pierceable seal (illustratively, a foil strip 180) that cover the upper opening 170, the first lower opening 172, and the second lower opening 174, respectively, to provide an initially sterile environment for the needle assembly 144. The needle assembly container 164 includes a coupling feature (illustratively, two upwardly extending arms 182) that couple the needle assembly container 164 to the coupling feature of the plunger restraint 58 (illustratively, the two T-shaped protrusions 74). In other embodiments, the needle assembly container 164 may have different structures.

Figure 29:
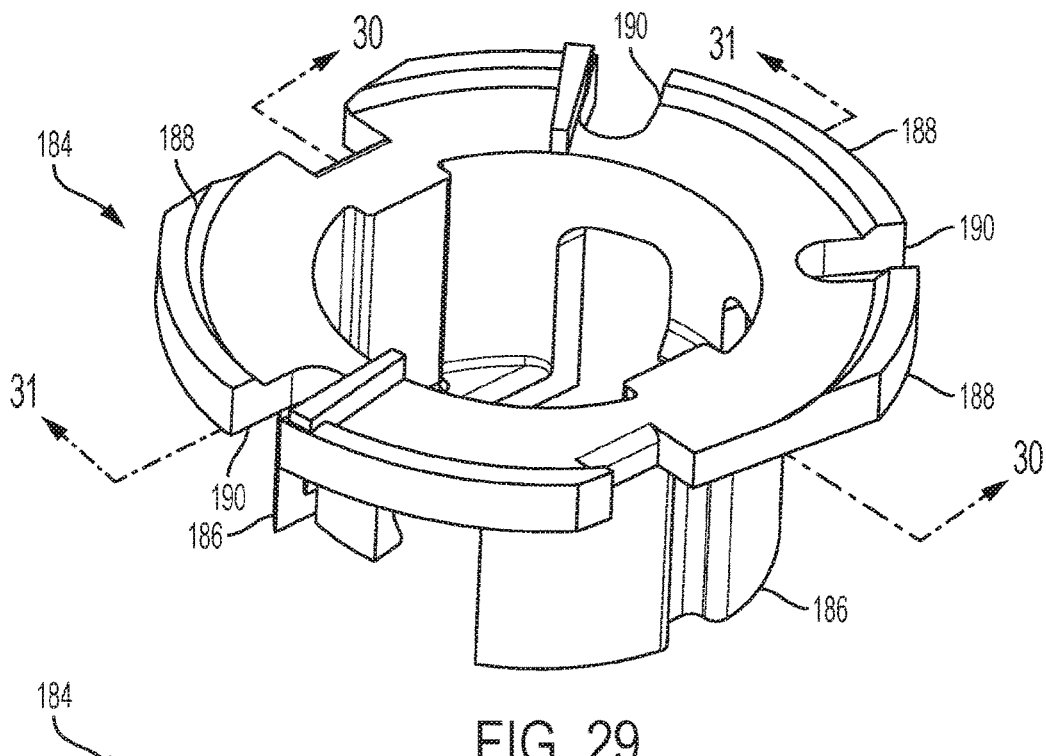
FIG. 29 is a top perspective view of a retraction frame of the therapeutic agent delivery device of FIG. 4.
Figure 30:
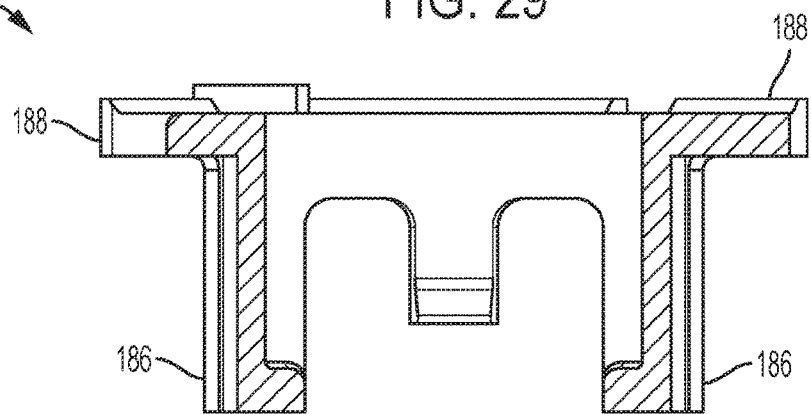
FIG. 30 is a side sectional view of the retraction frame along line 30-30 of FIG. 29.
Figure 31:
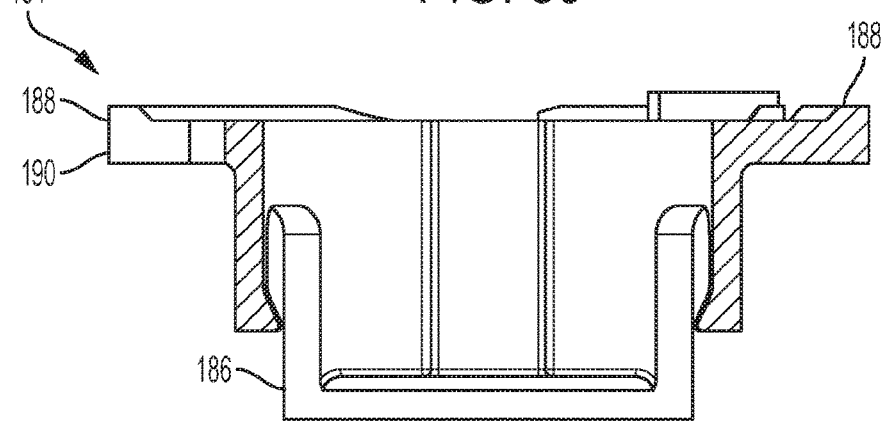
FIG. 31 is a front sectional view of the retraction frame along line 31-31 of FIG. 29.

FIGS. 29-31 illustrate a retraction frame 184 of the retraction mechanism 36. The retraction frame 184 includes a coupling feature (illustratively, two downwardly extending legs 186) that couple to the needle assembly container 164. The retraction frame 184 also includes a second restraint feature (illustratively, three partial flanges 188) that engages the first restraint feature of the drive wheel 38 (illustratively, the three axially extending arms 48) to inhibit translation of the retraction mechanism 36 relative to the housing 16.

Illustratively, channels 190 are disposed between the partial flanges 188. In other embodiments, the retraction frame 184 may have different structures. For example, in some embodiments positive features may be replaced with negative features, and vice versa. As another example, the retraction frame 184 could be monolithically formed with the needle assembly container 164.

Figure 33:
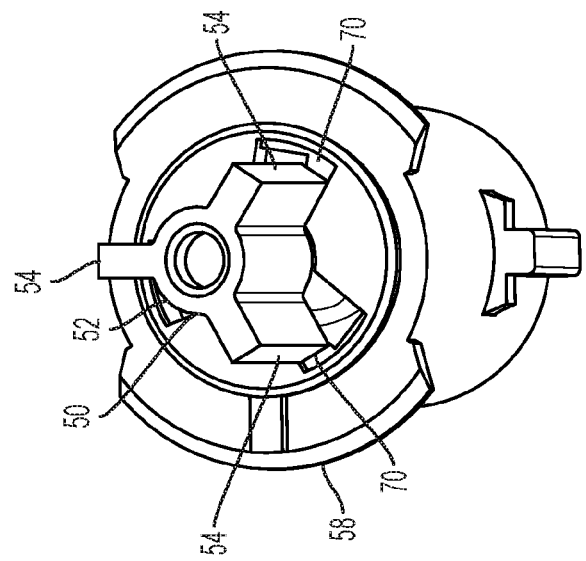
FIG. 33 is a perspective view of the plunger rod and the plunger restraint of the therapeutic agent delivery device of FIG. 4 in the initial configuration.
Figure 32:
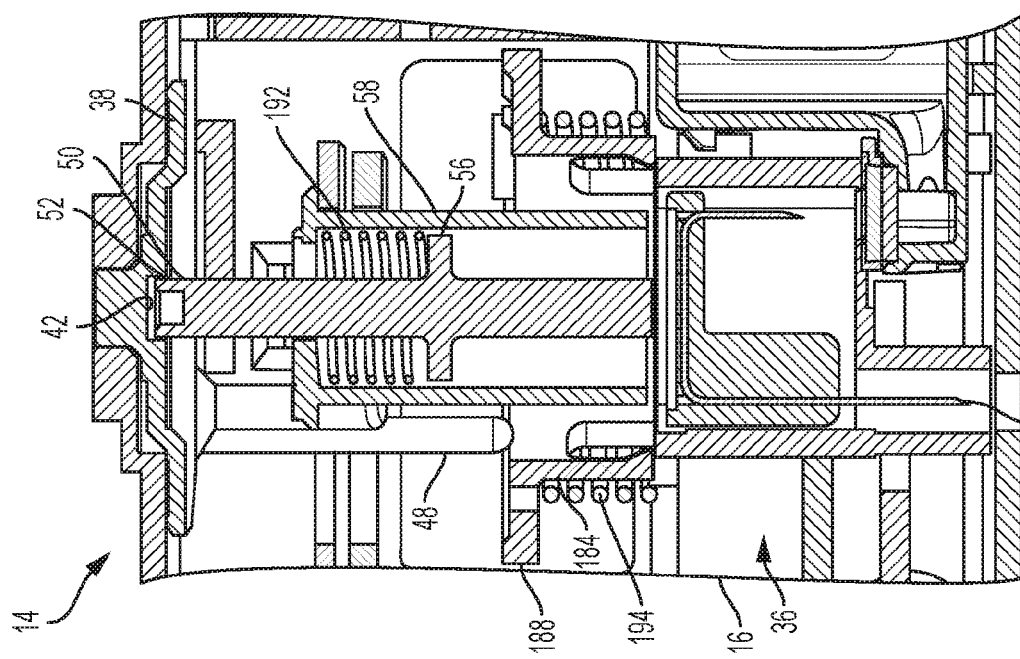
FIG. 32 is a front sectional view of the therapeutic agent delivery device of FIG. 4 in an initial configuration.

Illustratively, actuation of the therapeutic agent delivery device 14 is as follows. FIG. 32 illustrates the therapeutic agent delivery device 14 in an initial configuration, and FIG. 33 specifically illustrates the relative positions of the plunger rod 50 and the plunger restraint 58 in the initial configuration. In the initial configuration, the upper end portion 52 of the plunger rod 50 is disposed in the recess 42 of the drive wheel 38, and the plunger rod 50 and the drive wheel 38 are disposed in an initial rotational configuration (also referred to as a first rotational configuration). The ribs 54 of the plunger rod 50 are in engagement with the stop surfaces 70 of the plunger restraint 58, and the plunger rod 50 is disposed in an initial translational configuration (also referred to as a first translational configuration). A deployment spring 192, which is carried within the plunger restraint 58, is compressed between the flange 56 of the plunger rod 50 and the plunger restraint 58. The axially extending arms 48 of the drive wheel 38 are in engagement with the partial flanges 188 of the retraction frame 184, and the retraction mechanism 36 is disposed in an initial translational configuration (also referred to as a third translational configuration). A retraction spring 194 is compressed between the retraction frame 184 and the housing 16. In addition, the needle 30 is in a stowed configuration (illustratively, a configuration in which the needle 30 is disposed entirely within the housing 16.

Figure 35:
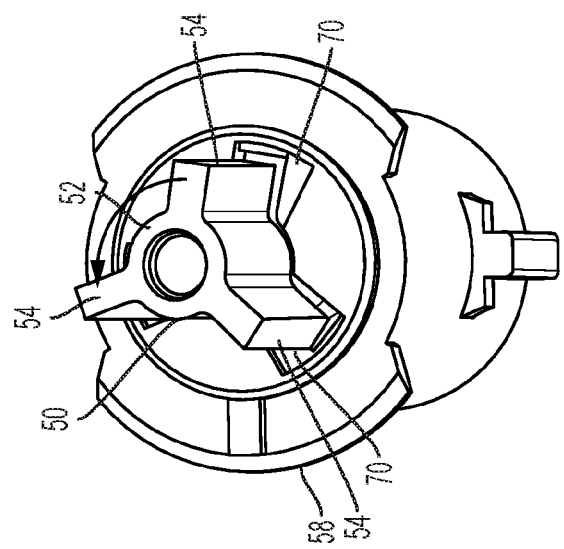
FIG. 35 is a perspective view of the plunger rod of the therapeutic agent delivery device of FIG. 4 being rotated from the first rotational configuration to the second rotational configuration relative to the plunger restraint.
Figure 34:
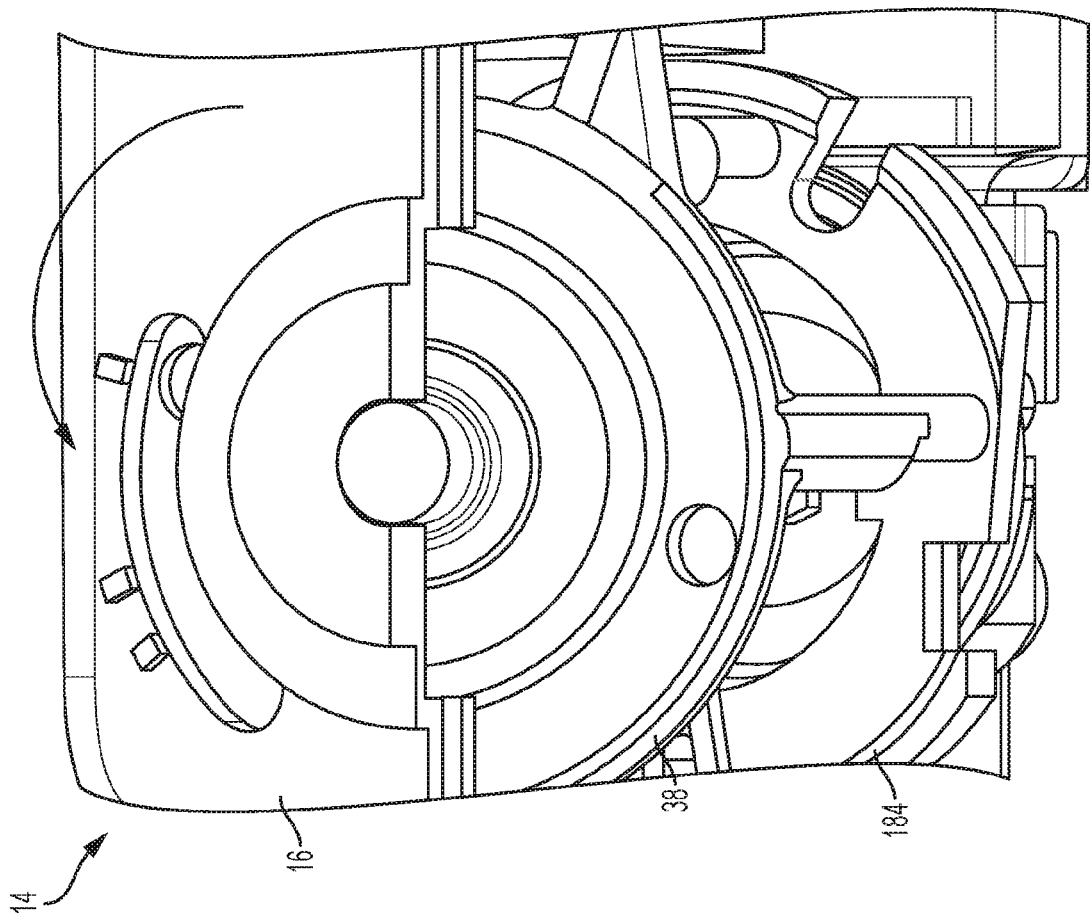
FIG. 34 is a partial perspective view of the drive wheel of the therapeutic agent delivery device of FIG. 4 being rotated from a first rotational configuration to a second rotational configuration; a portion of the housing is hidden to illustrate internal components.
Figure 36:
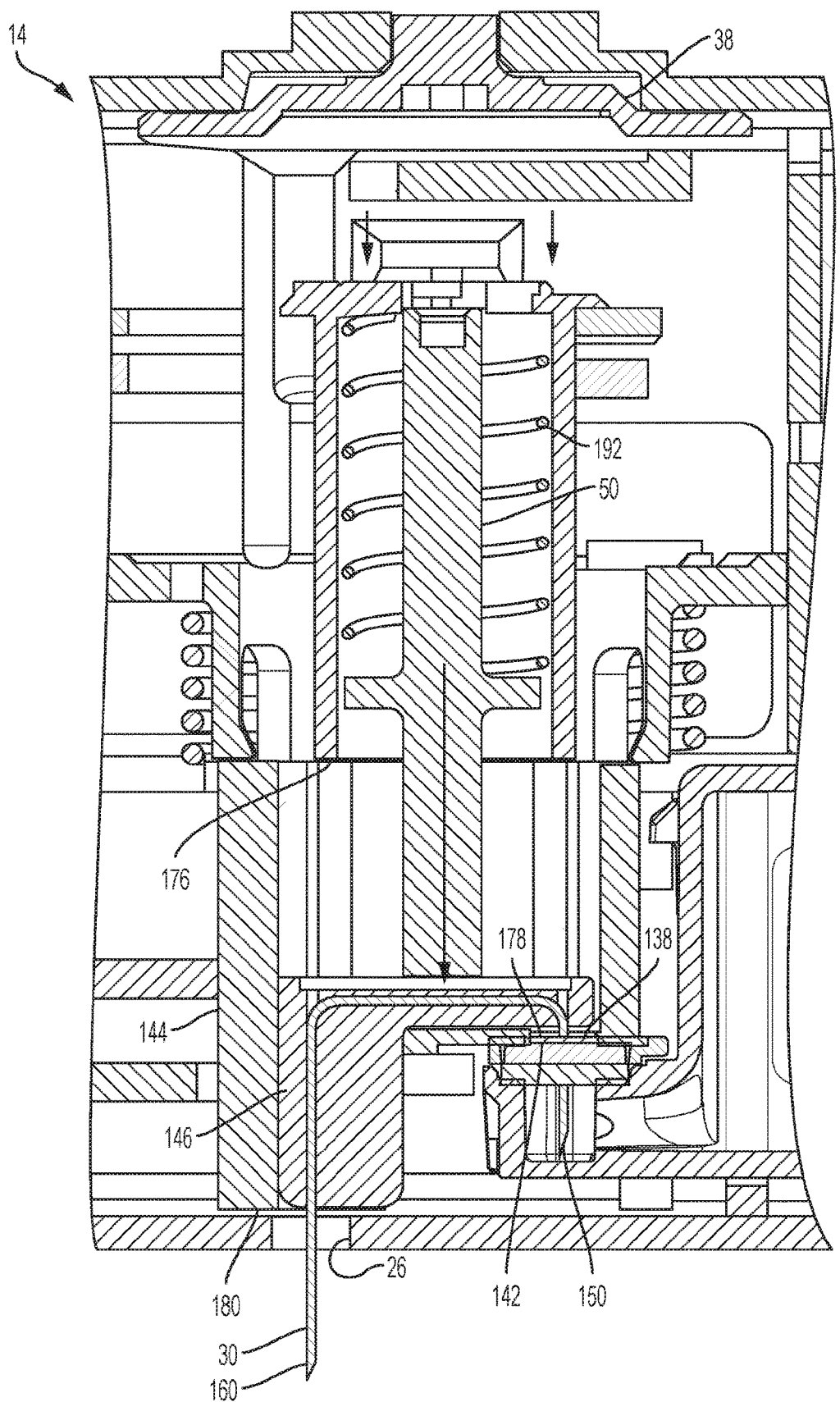
FIG. 36 is a front sectional view of the therapeutic agent delivery device of FIG. 4 with the plunger rod in a second rotational configuration and the needle in a deployed configuration.

FIG. 34 illustrates the drive wheel 38 being rotated to a second rotational configuration (for example, by the base device 12), and FIG. 35 specifically illustrates the plunger rod 50 being rotated to the second rotational configuration relative to the plunger restraint 58. The drive wheel 38 and the plunger rod 50 rotate together from the first rotational configuration to the second rotational configuration because the upper end portion 52 of the plunger rod 50 is initially received in the recess 42 of the drive wheel 38. As shown in FIG. 35, in the second rotational configuration the ribs 54 of the plunger rod 50 disengage (that is, are angularly misaligned with) the stop surfaces 70 of the plunger restraint 58. As a result, the deployment spring 192 is relatively unconstrained and, as shown in FIG. 36, the deployment spring 192 expands and translates the plunger rod 50 from the first translational configuration to a second translational configuration. When moving from the first translational configuration to the second translational configuration, the plunger rod 50 disengages the drive wheel 38, pierces the foil strip 176 of the needle assembly 144 carrier, engages the needle carrier 146, and pushes the needle carrier 146 such that the needle 30 translates from the stowed configuration to a deployed configuration. Illustratively, in the deployed configuration the needle inlet portion 150 extends through the foil strip 178 of the needle assembly 144, the foil strip 142 of the syringe assembly 126, and into the syringe outlet 138, and the needle outlet portion 160 extends through the foil strip 180 of the needle assembly 144 carrier, through the lower aperture 26 of the housing 16, and is at least partially disposed outside the housing 16.

Figure 37:
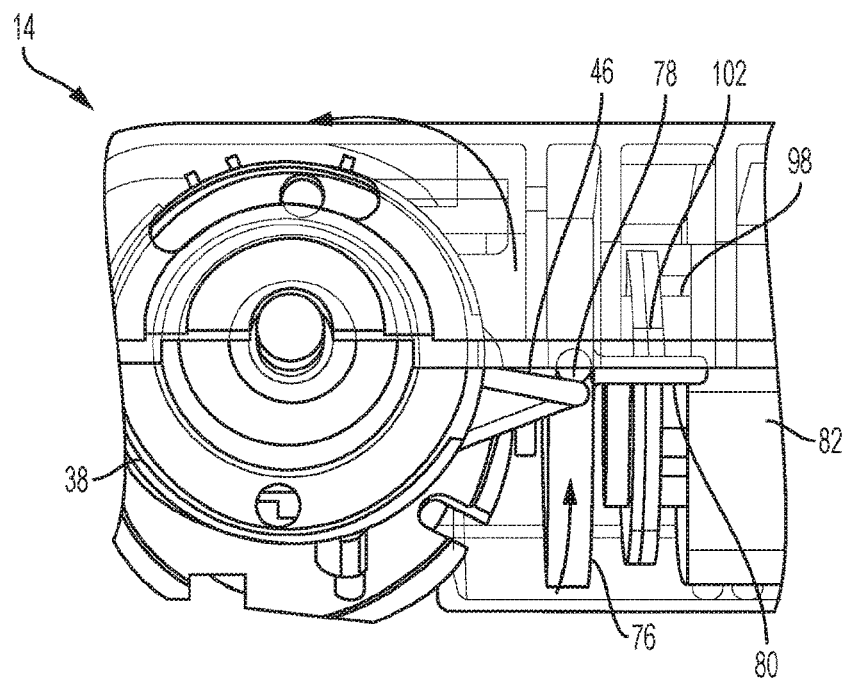
FIG. 37 is a partial perspective view of the drive wheel of the therapeutic agent delivery device of FIG. 4 being rotated past the second rotational configuration; a portion of the housing is hidden to illustrate internal components.
Figure 38:
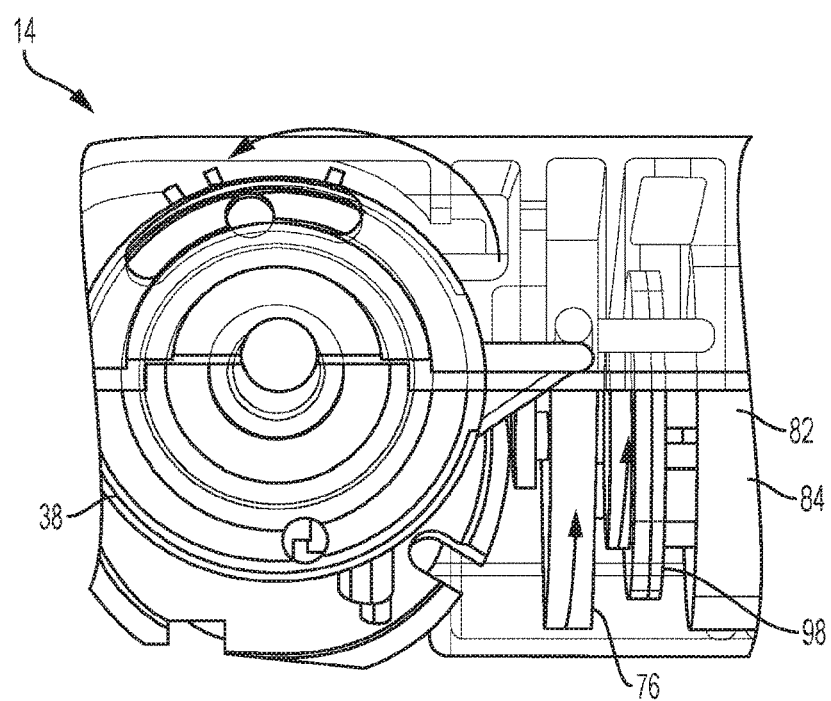
FIG. 38 is a partial perspective view of the drive wheel of the therapeutic agent delivery device of FIG. 4 being rotated further past the second rotational configuration and to a third rotational configuration, thereby rotating the activation wheel and the shuttle relative to the first and second mixing chambers of the pressure generating actuator; a portion of the housing is hidden to illustrate internal components.
Figure 39:
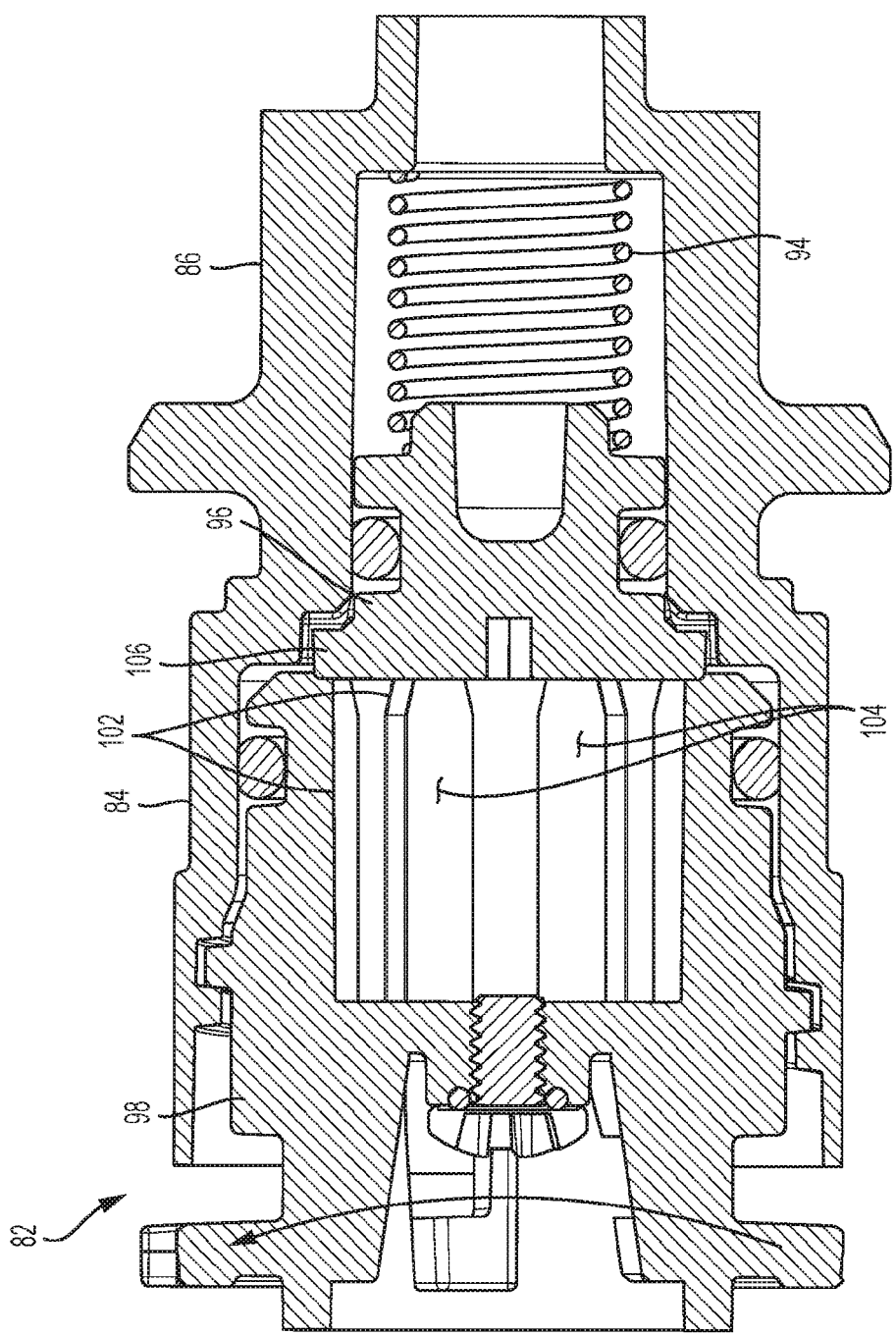
FIG. 39 is a longitudinal sectional view of the shuttle being rotated relative to the first and second mixing chambers of the pressure generating actuator.
Figure 40:
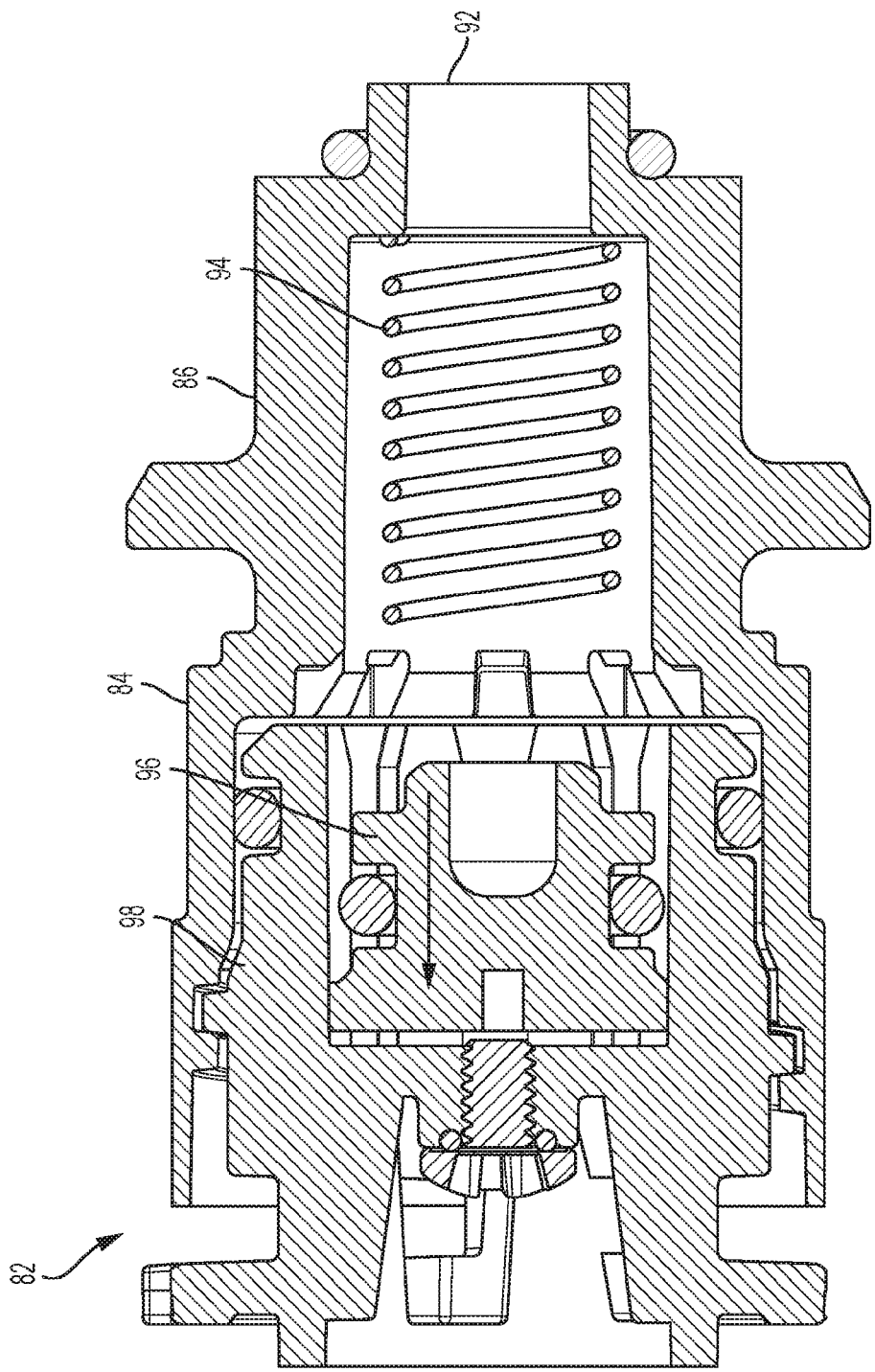
FIG. 40 is a longitudinal section view of the shuttle and a mixing piston of the therapeutic agent delivery device of FIG. 4 in an actuated configuration.

FIG. 37 illustrates the drive wheel 38 being rotated past the second rotational configuration such that the radially-outwardly extending arm 46 of the drive wheel 38 engages the radially-outwardly extending finger 78 of the activation wheel 76, and the axially-extending arms 80 of the activation wheel 76 engage the tabs 102 of the shuttle 98 of the pressure generating actuator 82. FIG. 38 illustrates the drive wheel 38 being rotated further past the second rotational configuration and to a third rotational configuration, the drive wheel 38 thereby rotating the activation wheel 76 and the shuttle 98 relative to the first mixing chamber 84 of the pressure generating actuator 82 (illustratively, by 22 degrees, although other angles may alternatively be used). Illustratively, the activation wheel 76 and the shuttle 98 rotate about an axis that is substantially perpendicular (that is, perpendicular±5 degrees) to the axis of the drive wheel 38. FIG. 39 specifically illustrates the shuttle 98 being rotated relative to the first and second mixing chambers 84, 86. Rotating the shuttle 98 relative to the first and second mixing chambers 84, 86 angularly misaligns the radially-inwardly extending tabs 102 of the shuttle 98 with the radially-outwardly extending tabs 106 of the mixing piston 96 and angularly aligns the channels 104 of the shuttle 98 with the radially-outwardly extending tabs 106 of the mixing piston 96. As a result, the actuator spring 94 is relatively unconstrained and, as shown in FIG. 40, the actuator spring 94 expands and translates the mixing piston 96 into the shuttle 98 and the first mixing chamber 84. The reagents in the first mixing chamber 84 and the second mixing chamber 86 then mix and react to provide a pressurized gas, which the pressure generating actuator 82 delivers from the actuator outlet 92.

Figure 41:
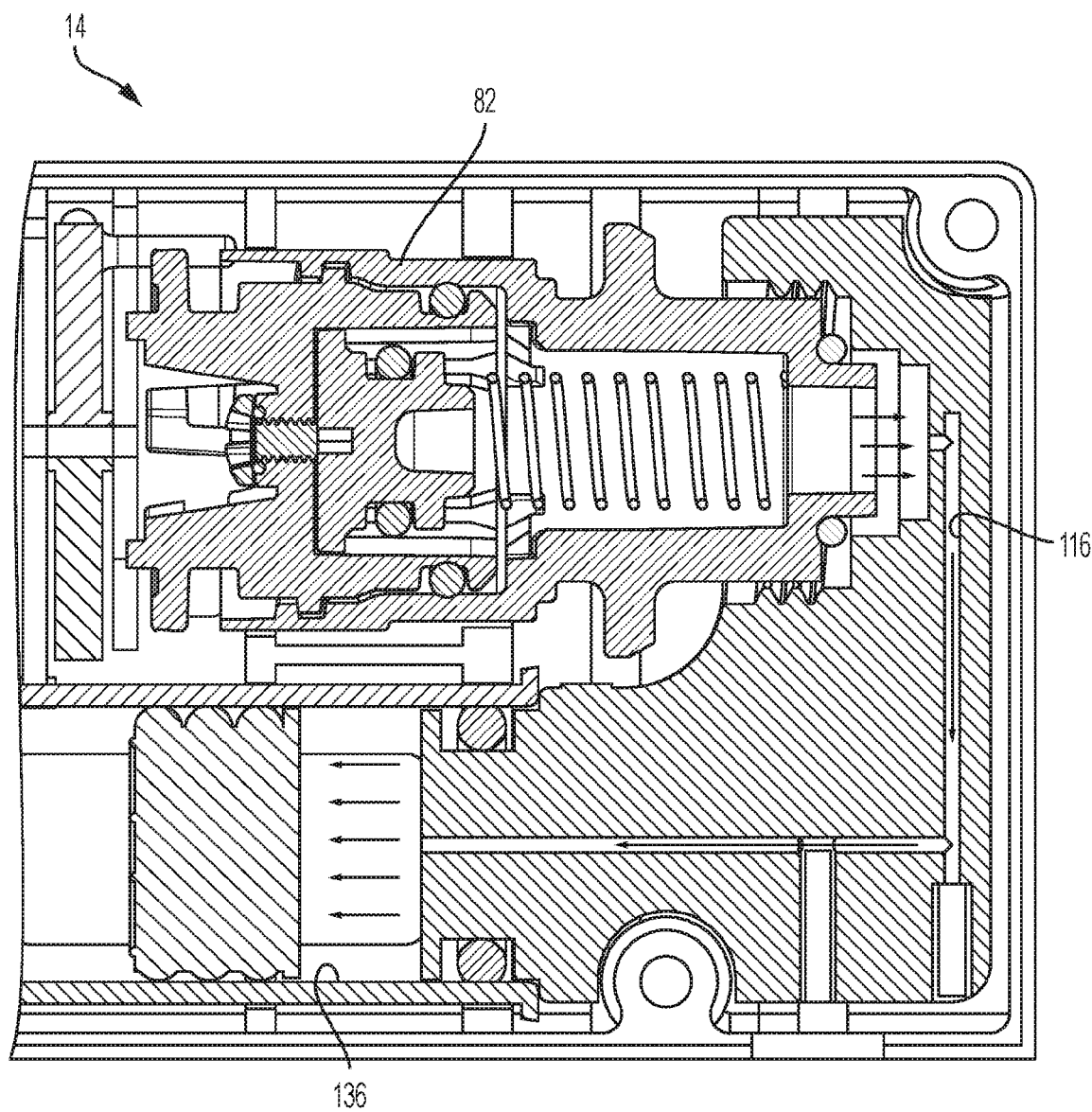
FIG. 41 is a front sectional view of the therapeutic agent delivery device of FIG. 4 with the pressure generating actuator delivering a pressurized gas through a manifold and to a syringe assembly.
Figure 42:
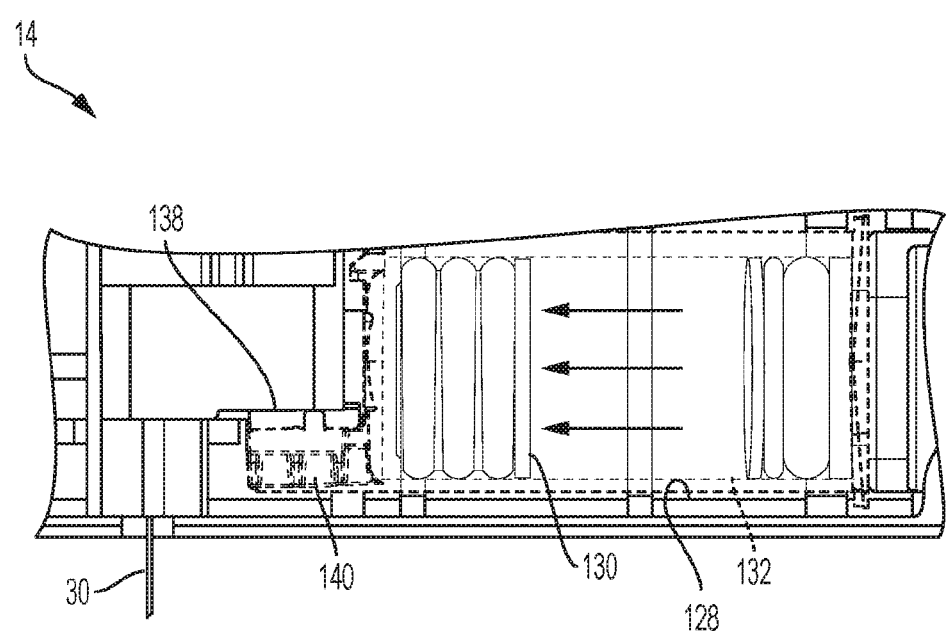
FIG. 42 is a front view of the therapeutic agent delivery device of FIG. 4 and the pressurized gas translating a syringe piston of the syringe assembly; a portion of the housing is hidden to illustrate internal components.

FIG. 41 illustrates the pressure generating actuator 82 delivering the pressurized gas through the manifold passageway 116 and to the syringe passageway 136. As shown in FIG. 42, the pressurized gas translates the syringe piston 130 away from the syringe inlet portion 132 and toward the syringe outlet portion 140. As a result, the syringe chamber 128 delivers the therapeutic agent through the syringe outlet 138 and to the needle 30. The needle 30 discharges and delivers the therapeutic agent to the subject.

Figure 44:
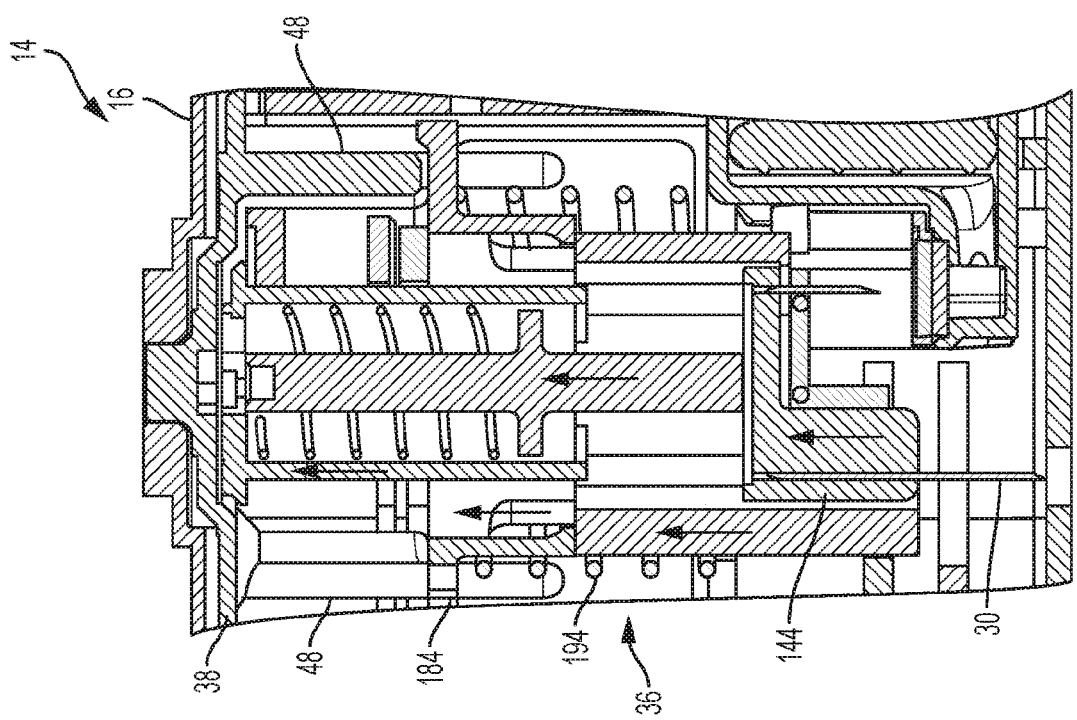
FIG. 44 is a front sectional view of the drive wheel being rotated to the fourth rotational configuration and the retraction mechanism moving from the initial translational configuration to the retracted translational configuration.
Figure 43:
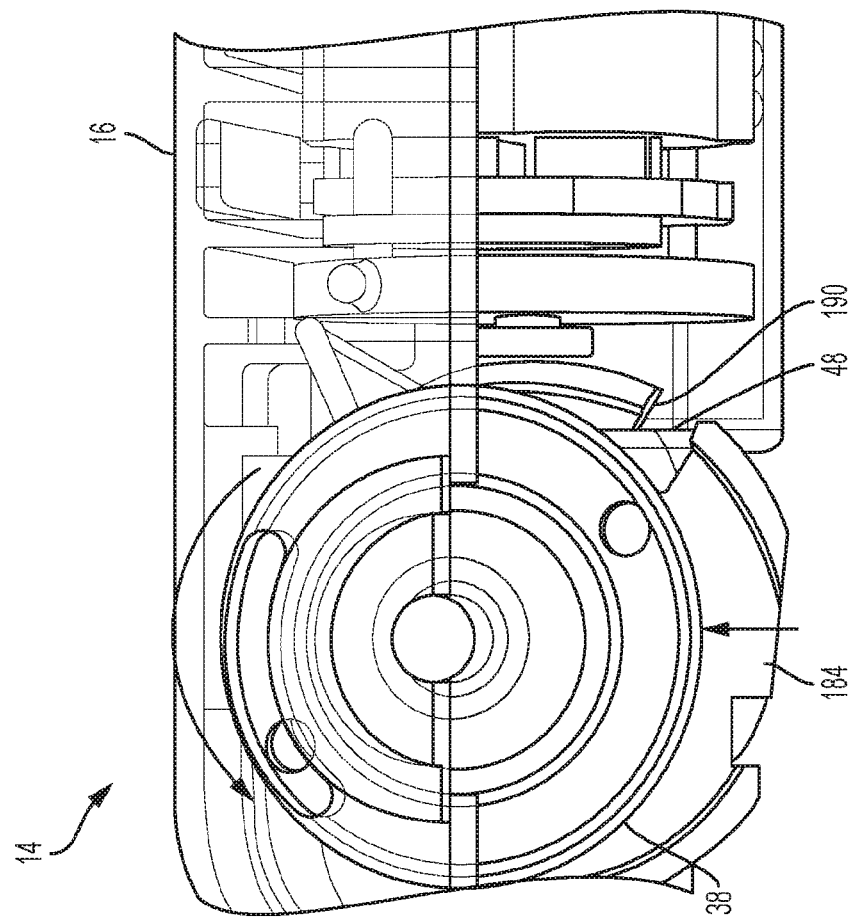
FIG. 43 is a partial perspective view of the drive wheel of the therapeutic agent delivery device of FIG. 4 being rotated to a fourth rotational configuration and the retraction mechanism moving from an initial translational configuration to a retracted translational configuration; a portion of the housing is hidden to illustrate internal components.

Illustratively, the drive wheel 38 temporarily stops rotating while the needle 30 delivers the therapeutic agent to the subject. Thereafter, the drive wheel 38 continues rotating until it reaches a fourth rotational configuration, as shown in FIGS. 43 and 44. In the fourth rotational configuration, the axially extending arms 48 of the drive wheel 38 are angularly aligned with the channels 190 in the retraction frame 184. As a result, the retraction spring 194 is relatively unconstrained and the retraction spring 194 expands and translates the retraction mechanism 36 from its initial translational configuration to a retracted translational configuration (also referred to as a fourth translational configuration). Translation of the retraction mechanism 36 from the initial translational configuration to the retracted translational configuration translates the needle assembly 144 from the deployed configuration to a withdrawn configuration (illustratively, a configuration in which the needle 30 is entirely disposed within the housing 16). Illustratively, translation of the retraction mechanism 36 from the initial translational configuration to the retracted translational configuration inhibits further rotation of the drive wheel 38 relative to the housing 16. Illustratively, the therapeutic agent delivery device 14 may then be discarded.

B. Base Device

Figure 45:
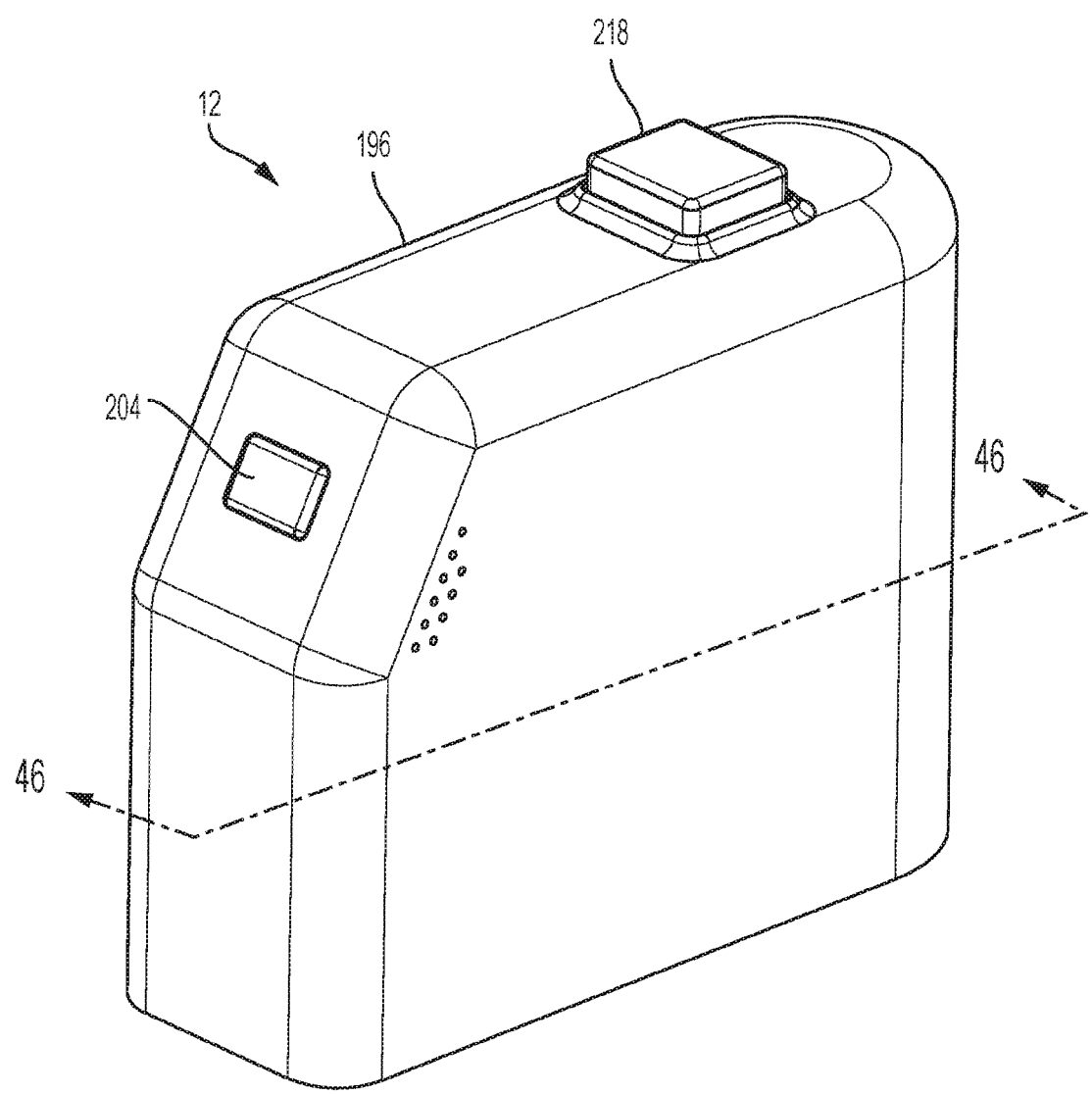
FIG. 45 is a top perspective view of the base device of the therapeutic agent delivery system of FIG. 1.
Figure 46:
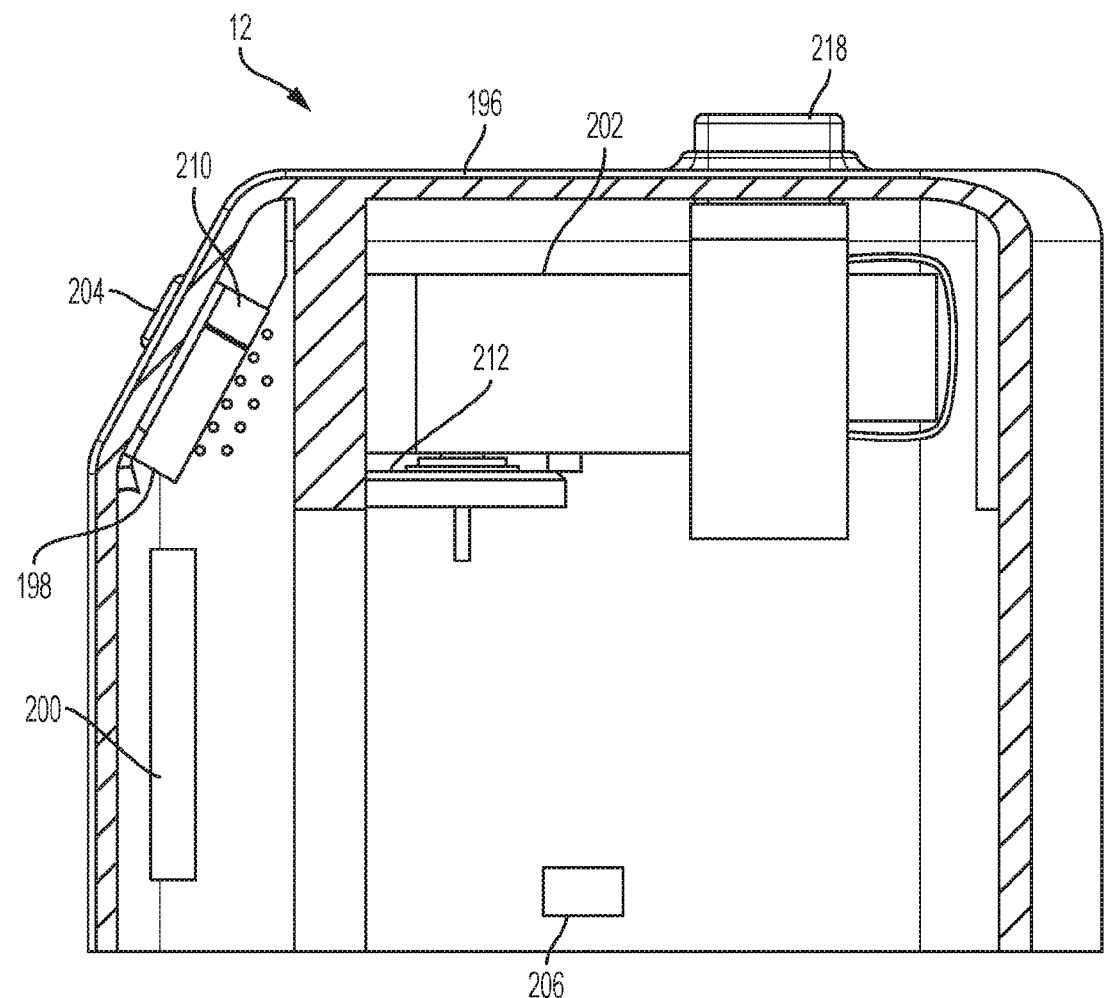
FIG. 46 is a front sectional view of the base device of FIG. 45.
Figure 47:
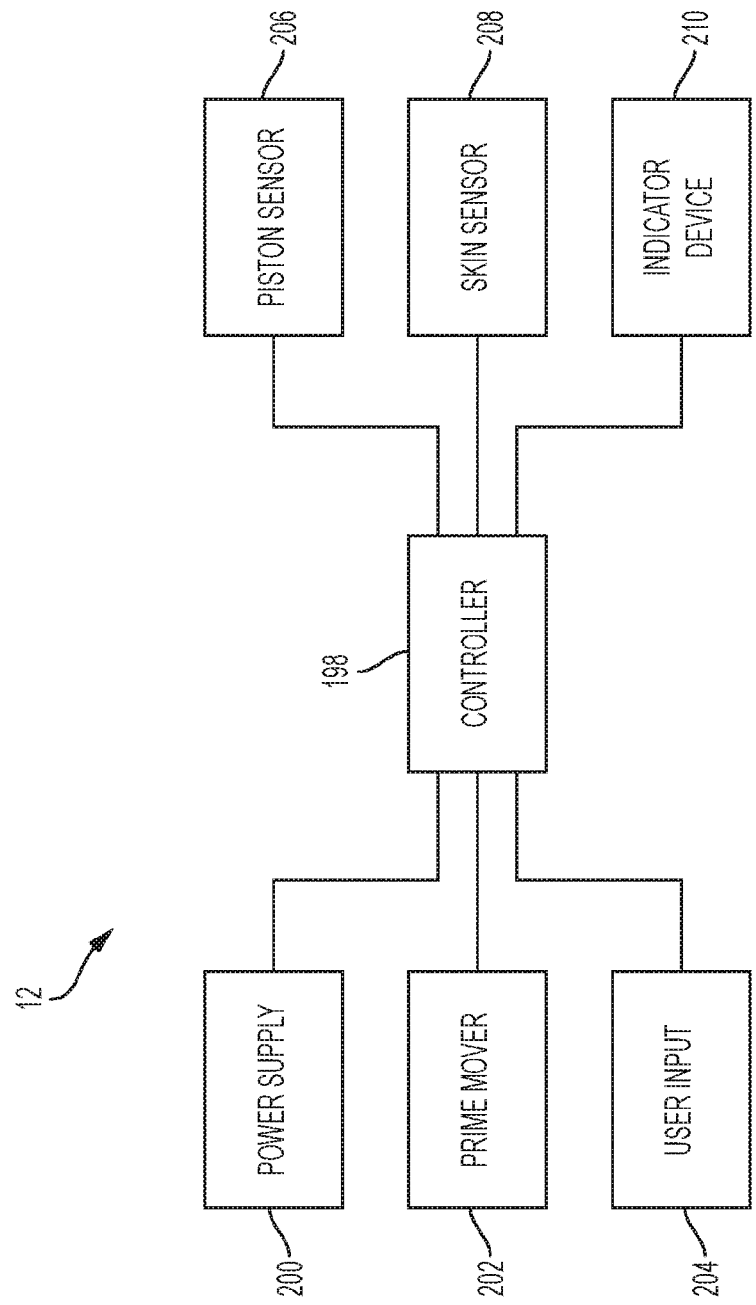
FIG. 47 is a schematic representation of electronic components of the base device of FIG. 45.
Figure 48:
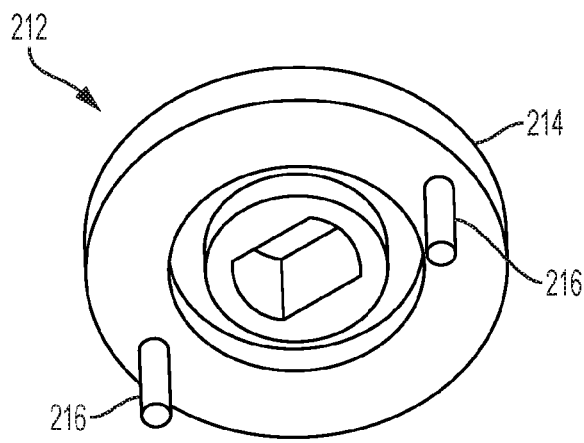
FIG. 48 is a top perspective view of an output wheel of the base device of FIG. 45.

FIGS. 45-46 illustrate the base device 12 of the therapeutic agent delivery system 10. FIG. 47 schematically illustrates electronic components of the base device 12. The base device 12 includes a housing 196 that carries various components. The housing 196 illustratively includes a monolithic structure, although in other embodiments the housing 196 may include two or more separately formed portions. The base device 12 includes an electronic controller 198 that is operatively coupled to and receives power from a power supply 200 (illustratively, a rechargeable battery). In some embodiments, the controller 198 wirelessly communicates with a remote device (not shown—for example, a server or a mobile telephone via Bluetooth or the like). The controller 198 may, for example, receive operating instructions from the remote device or send data to the remote device. The controller 198 is operatively coupled to a prime mover 202 (illustratively, an electric motor) that detachably couples to and actuates the therapeutic agent delivery device 14. The controller 198 is operatively coupled to a user input 204 (illustratively, a depressible button). The user input 204 may be actuated, illustratively, to energize the prime mover 202 and thereby actuate the therapeutic agent delivery device 14 and deliver a therapeutic agent to a subject. The controller 198 is operatively coupled to a piston sensor 206 that is configured to determine the position of the syringe piston 130 in the syringe chamber 128 (for example, to determine if the syringe piston 130 has been moved toward the syringe outlet 138, thereby indicating that the therapeutic agent has been delivered to the subject and the needle 30 should be moved from the deployed configuration to the withdrawn configuration). Illustratively, the piston sensor 206 is a hall effect sensor that is configured to sense a magnet carried by the syringe piston 130 (not shown). In other embodiments, the sensor is an optical sensor. The controller 198 is operatively coupled to a skin sensor 208 that is configured to sense the presence of a conductive surface (for example, the subject's skin). The controller 198 may inhibit actuation of the therapeutic agent delivery device 14 if the skin sensor 208 does not sense the presence of a conductive surface. The controller 198 is operatively coupled to an indicator device 210 (including, for example, visual and/or audible indicators). Illustratively, the indicator device 210 indicates if the therapeutic agent has been delivered to the subject (for example, based on information provided to the controller 198 by the piston sensor 206).

Figure 49:
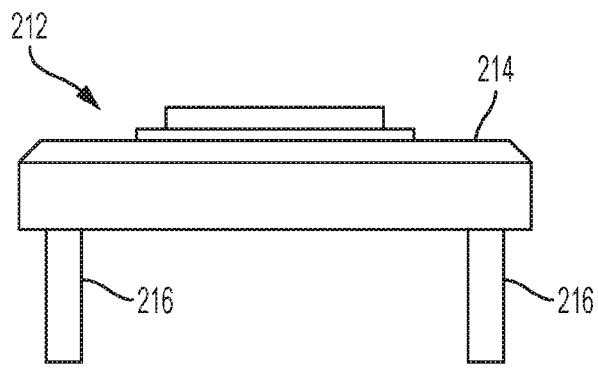
FIG. 49 is a side view of the output wheel of FIG. 48.
Figure 50:
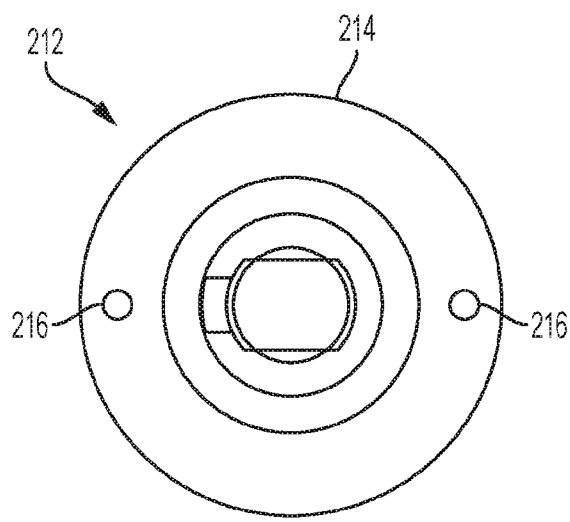
FIG. 50 is a bottom view of the output wheel of FIG. 48.

FIGS. 49-50 illustrate an output wheel 212 of the prime mover 202 of the base device 12. The output wheel 212 includes a main body 214 that carries one or more coupling features (illustratively, two axially extending arms 216) that facilitate coupling the base device 12 to the therapeutic agent delivery device 14. Illustratively, the axially extending arms 216 are removeably received in the apertures of the drive wheel 38 to facilitate rotating the drive wheel 38 within the housing 16.

Figure 52:
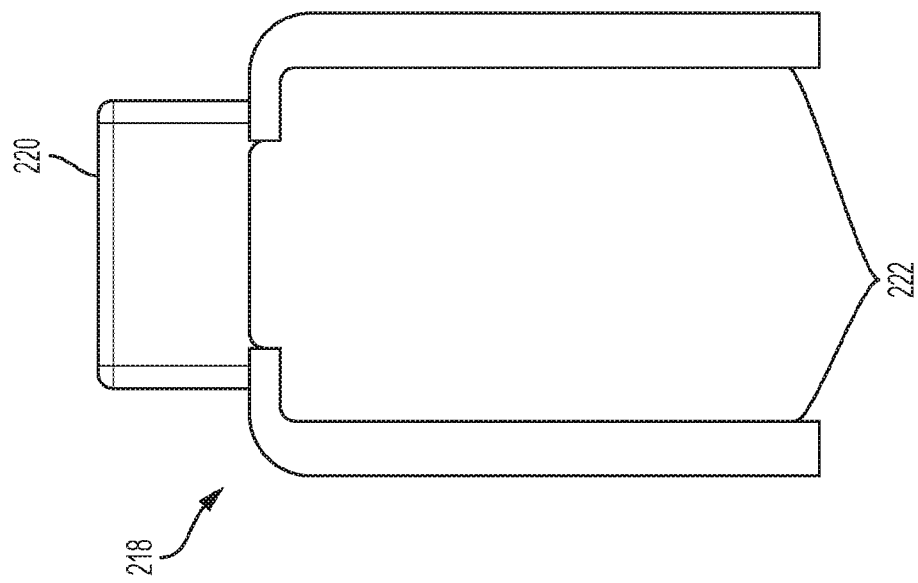
FIG. 52 is a side view of the ejector component of FIG. 51.
Figure 51:
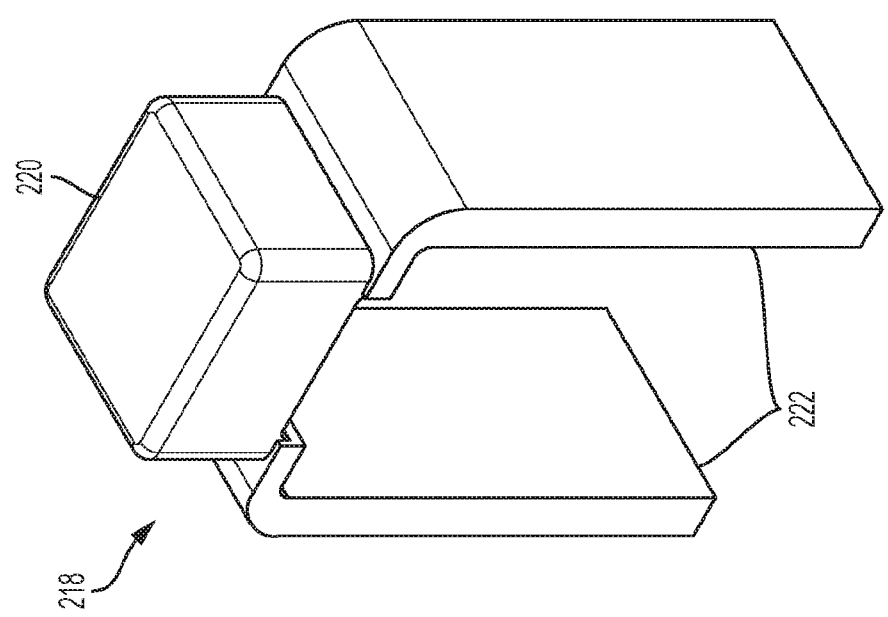
FIG. 51 is a top perspective view of an ejector component of the base device of FIG. 45.

FIGS. 51-52 illustrate an ejector component 218 of the base device 12. The ejector component 218 is translatably carried by the housing 196 of the base device 12. The ejector component 218 includes an exposed portion 220 that may be pressed by a user to translate the ejector component 218 relative to the housing 196. The exposed portion 220 is coupled to two ejector legs 222. The ejector legs 222 are configured to engage and push a therapeutic agent delivery device 14 from the housing 196 of the base device 12 when the exposed portion 220 is pressed. The housing 196 of the base device 12 may then be reloaded with a new therapeutic agent delivery device 14.

C. Exemplary Alternative Embodiments

Figure 53:
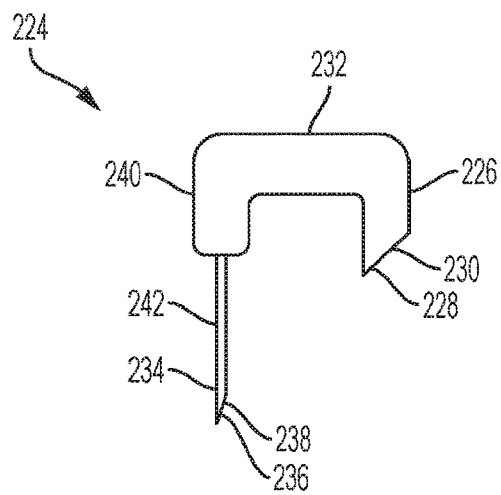
FIG. 53 is a front view of a needle according to another embodiment of the present disclosure.

FIG. 53 illustrates a needle 224 according to an embodiment of the present disclosure. The needle 224 may be used, for example, in the therapeutic agent delivery device 14 instead of the needle 30. The needle 224 is generally similar to the needle 30. That is, the needle 224 includes an inlet portion 226 (having a first piercing tip 228 and an inlet 230), a needle passageway (not shown), a connection portion 232, and an outlet portion 234 (having a second piercing tip 236 and an outlet 238). In contrast to the needle 30, however, the portion of the needle passageway within the inlet portion 226, the connection portion 232, an upper section 240 of the outlet portion 234 has a relatively large diameter compared to that of the needle passageway within a lower section 242 of the outlet portion 234. In some embodiments, the larger diameter is substantially 50 percent larger than the smaller diameter (that is, 50 percent larger±5 percent). In some embodiments, the needle 224 facilitates relatively rapidly delivering a therapeutic agent to a subject.

Figure 54:
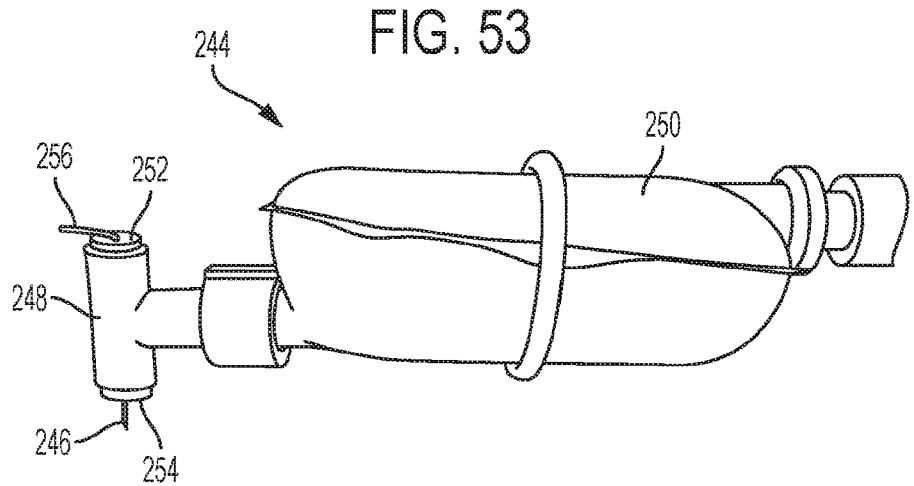
FIG. 54 is a front view of a bladder assembly and a needle according to another embodiment of the present disclosure.
Figure 55:
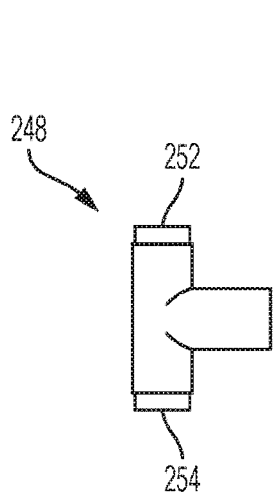
FIG. 55 is a front view of a double-septum component of the bladder assembly of FIG. 54.
Figure 56:
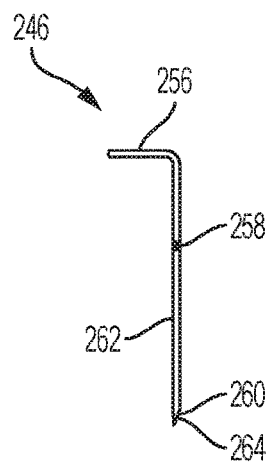
FIG. 56 is a front view of the needle of FIG. 54.

FIG. 54 illustrates a bladder assembly 244 and a needle 246 according to an embodiment of the present disclosure. FIG. 55 illustrates a double-septum component 248 of the bladder assembly 244. FIG. 56 illustrates the needle 246. The bladder assembly 244 and the needle 246 may be used, for example, in the therapeutic agent delivery device 14 instead of the syringe assembly 126 and the needle 30. The bladder assembly 244 includes a compressible bladder 250 that carries a therapeutic agent. The compressible bladder 250 is in communication with and delivers the therapeutic agent to the double-septum component 248. The double-septum component 248 and the needle 246 may initially be contained in a sterile carrier (not shown). The double-septum component 248 includes a first, or upper, seal (illustratively, a foil strip 252) through which the needle 246 extends. The double-septum component 248 also includes a second, or lower, seal (illustratively, a foil strip 254) that the needle 246 pierces and through which the needle 246 extends in a deployed configuration (that is, as shown in FIG. 54). The needle 246 includes a closed end portion (illustratively, a bent portion 256; in other embodiments, a straight portion) and inlet 258 formed in the side of the needle 246. The inlet 258 is disposed within the double-septum component 248 and receives the therapeutic agent therefrom. The inlet 258 may initially be obscured by a fitting within the double-septum component 248 (not shown). The needle 246 includes a passageway (not shown) in communication with the inlet 258, and the passageway is also in communication with an outlet 260 at an outlet portion 262 of the needle 246. The outlet 260 discharges the therapeutic agent from the needle 246. The outlet portion 262 also includes a piercing tip 264 that pierces the lower seal and the skin of the user.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A therapeutic agent delivery system, comprising:
a housing;
a drive wheel carried by the housing, the drive wheel being rotatable relative to the housing;
a plunger rod being rotatable with the drive wheel relative to the housing from a first rotational configuration to a second rotational configuration, and the plunger rod being translatable relative to the housing from a first translational configuration to a second translational configuration;
a plunger restraint maintaining the plunger rod in the first translational configuration when the plunger rod is disposed in the first rotational configuration, and the plunger restraint permitting the plunger rod to translate to the second translational configuration when the plunger rod is disposed in the second rotational configuration;
a needle being movable relative to the housing from a stowed configuration to a deployed configuration, and the needle being moved from the stowed configuration to the deployed configuration by the plunger rod when the plunger rod moves from the first translational configuration to the second translational configuration; and
a therapeutic agent delivery assembly carrying a therapeutic agent and in communication with the needle, and the therapeutic agent delivery assembly being actuated by rotation of the drive wheel relative to the housing and thereby delivering the therapeutic agent to the needle.

2. The therapeutic agent delivery system of claim 1, wherein the drive wheel is rotatable relative to the housing from the first rotational configuration to the second rotational configuration, and the second rotational configuration to a third rotational configuration, the therapeutic agent delivery assembly being actuated and delivering the therapeutic agent to the needle when the drive wheel rotates from the second rotational configuration to the third rotational configuration.

3. The therapeutic agent delivery system of claim 1, further comprising a spring urging the plunger rod to translate from the first translational configuration to the second translational configuration.

4. The therapeutic agent delivery system of claim 1, wherein the plunger rod is partially carried within the plunger restraint, the plunger rod extends through a first end portion of the plunger restraint in the first translational configuration, and the plunger rod extends through a second end portion of the plunger restraint in the second translational configuration.

5. The therapeutic agent delivery system of claim 4, further comprising a spring carried within the plunger restraint, the spring urging the plunger rod to translate from the first translational configuration to the second translational configuration.

6. The therapeutic agent delivery system of claim 4, wherein the plunger rod comprises a first restraint feature, the plunger restraint comprises a second restraint feature, and the first restraint feature and the second restraint feature engage each other when the plunger rod is disposed in the first rotational configuration to inhibit the plunger rod from translating from the first translational configuration to the second translational configuration.

7. The therapeutic agent delivery system of claim 1, wherein the needle is movable relative to the housing from the deployed configuration to a withdrawn configuration, and further comprising a retraction mechanism being translatable relative to the housing from a third translational configuration to a fourth translational configuration, the retraction mechanism moving the needle from the deployed configuration to the withdrawn configuration when moving from the third translational configuration to the fourth translational configuration.

8. The therapeutic agent delivery system of claim 7, wherein the drive wheel comprises a first restraint feature, the retraction mechanism comprises a second restraint feature, and the first restraint feature and the second restraint feature engage each other in the first rotational configuration and the second rotational configuration to inhibit the retraction mechanism from moving from the third translational configuration to the fourth translational configuration.

9. The therapeutic agent delivery system of claim 7, further comprising a spring urging the retraction mechanism to translate from the third translational configuration to the fourth translational configuration and thereby urging the needle to move to the withdrawn configuration.

10. The therapeutic agent delivery system of claim 1, further comprising a base device detachably carrying the housing, the base device comprising a prime mover being actuatable to rotate the drive wheel relative to the housing.

11. A therapeutic agent delivery system, comprising:
a housing;
a drive wheel carried by the housing, the drive wheel being rotatable relative to the housing from a first rotational configuration to a second rotational configuration;
a plunger rod being rotatable with the drive wheel relative to the housing from the first rotational configuration to the second rotational configuration, and the plunger rod being translatable relative to the housing from a first translational configuration to a second translational configuration;
a plunger restraint maintaining the plunger rod in the first translational configuration when the plunger rod is disposed in the first rotational configuration, and the plunger restraint permitting the plunger rod to translate to the second translational configuration when the plunger rod is disposed in the second rotational configuration;
a needle being movable relative to the housing from a stowed configuration to a deployed configuration, and from the deployed configuration to a withdrawn configuration, the needle being moved from the stowed configuration to the deployed configuration by the plunger rod when the plunger rod moves from the first translational configuration to the second translational configuration;
a therapeutic agent delivery assembly carrying a therapeutic agent and in fluid communication with the needle; and
a retraction mechanism being translatable relative to the housing from a third translational configuration to a fourth translational configuration, the retraction mechanism moving the needle from the deployed configuration to the withdrawn configuration when moving from the third translational configuration to the fourth translational configuration.

12. The therapeutic agent delivery system of claim 11, wherein the needle moves relative to the retraction mechanism when moving from the stowed configuration to the deployed configuration.

13. The therapeutic agent delivery system of claim 11, wherein the drive wheel comprises a first restraint feature, the retraction mechanism comprises a second restraint feature, and the first restraint feature and the second restraint feature engage each other in the first rotational configuration and the second rotational configuration to inhibit the retraction mechanism from moving from the third translational configuration to the fourth translational configuration.

14. The therapeutic agent delivery system of claim 13, wherein the drive wheel is rotatable relative to the housing from the second rotational configuration to a third rotational configuration, and rotation of the drive wheel from the second rotational configuration to the third rotational configuration causes the therapeutic agent delivery assembly to deliver the therapeutic agent to the needle.

15. The therapeutic agent delivery system of claim 14, wherein the drive wheel is rotatable relative to the housing from the third rotational configuration to a fourth rotational configuration, wherein the first restraint feature and the second restraint feature disengage each other in the fourth rotational configuration to permit the retraction mechanism to move from the third translational configuration to the fourth translational configuration and thereby move the needle to the withdrawn configuration.

16. The therapeutic agent delivery system of claim 15, further comprising a spring urging the retraction mechanism to translate from the third translational configuration to the fourth translational configuration and thereby urging the needle to move to the withdrawn configuration.

17. A therapeutic agent delivery system, comprising:
a housing;
a needle carried by the housing;
a therapeutic agent delivery assembly carrying a therapeutic agent and in fluid communication with the needle; and
a drive wheel carried by the housing and rotatable to:
a first rotational configuration in which the needle is in a stowed configuration relative to the housing;
a second rotational configuration in which the needle is in a deployed configuration relative to the housing;
a third rotational configuration in which the therapeutic agent delivery assembly delivers the therapeutic agent to the needle; and
a fourth rotational configuration in which the needle is in a withdrawn configuration relative to the housing.

18. The therapeutic agent delivery system of claim 17, wherein the therapeutic agent delivery assembly comprises a first mixing chamber and a second mixing chamber, wherein:
in the first and second rotational configurations, the first mixing chamber contains a first reagent and the second mixing chamber contains a second reagent; and
in the third rotational configuration, the first and second reagents mix and generate a pressurized fluid.

19. The therapeutic agent delivery system of claim 17, further comprising a prime mover removably coupled to the drive wheel and configured to rotate the drive wheel between the first, second, third, and fourth rotational configurations.

20. The therapeutic agent delivery system of claim 17, wherein the therapeutic agent delivery assembly is oriented substantially perpendicularly relative to the needle.

* * * * *